(12) United States Patent
Furuta et al.

(10) Patent No.: US 11,974,730 B2
(45) Date of Patent: *May 7, 2024

(54) MINIMALLY-INVASIVE MEASUREMENT OF ESOPHAGEAL INFLAMMATION

(71) Applicants: THE REGENTS OF THE UNIVERSITY OF COLORADO, Denver, CO (US); THE BOARD OF TRUSTEES OF THE UNIVERSITY OF ILLINOIS, Urbana, IL (US)

(72) Inventors: Glenn T. Furuta, Aurora, CO (US); Steven J. Ackerman, Naperville, IL (US)

(73) Assignees: The Regents of the University of Colorado, Denver, CO (US); The Board of Trustees of the University of Illinois, Urbana, IL (US)

(*) Notice: Subject to any disclaimer, the term of this patent is extended or adjusted under 35 U.S.C. 154(b) by 476 days.

This patent is subject to a terminal disclaimer.

(21) Appl. No.: 16/871,987

(22) Filed: May 11, 2020

(65) Prior Publication Data

US 2020/0352430 A1 Nov. 12, 2020

Related U.S. Application Data

(63) Continuation of application No. 15/964,839, filed on Apr. 27, 2018, now Pat. No. 10,674,901, which is a continuation of application No. 15/158,351, filed on May 18, 2016, now Pat. No. 9,980,634, which is a continuation of application No. 14/136,811, filed on Dec. 20, 2013, now Pat. No. 9,372,186, which is a continuation of application No. 12/741,549, filed as application No. PCT/US2008/082482 on Nov. 5, 2008, now Pat. No. 8,637,239.

(60) Provisional application No. 60/985,386, filed on Nov. 5, 2007.

(51) Int. Cl.

| | |
|---|---|
| A61B 1/273 | (2006.01) |
| A61B 1/00 | (2006.01) |
| A61K 31/437 | (2006.01) |
| A61K 31/4375 | (2006.01) |
| C12Q 1/04 | (2006.01) |
| C12Q 1/527 | (2006.01) |
| C12Q 1/6883 | (2018.01) |
| G01N 33/53 | (2006.01) |
| G01N 33/68 | (2006.01) |

(52) U.S. Cl.
CPC ........ *A61B 1/2733* (2013.01); *A61B 1/00156* (2013.01); *A61K 31/437* (2013.01); *A61K 31/4375* (2013.01); *C12Q 1/04* (2013.01); *C12Q 1/527* (2013.01); *C12Q 1/6883* (2013.01); *C12Y 406/01002* (2013.01); *G01N 33/5308* (2013.01); *G01N 33/6863* (2013.01); *G01N 33/6866* (2013.01); *G01N 33/6869* (2013.01); *G01N 33/6893* (2013.01); *G01N 2333/521* (2013.01); *G01N 2333/988* (2013.01); *G01N 2800/14* (2013.01); *G01N 2800/7028* (2013.01); *G01N 2800/7095* (2013.01); *Y02A 90/10* (2018.01)

(58) Field of Classification Search
CPC ............ A61B 1/2733; A61B 1/00156; A61K 31/437; A61K 31/4375; C12Q 1/04; C12Q 1/527; C12Q 1/6883; C12Y 406/01002; G01N 33/5308; G01N 33/6863; G01N 33/6866; G01N 33/6869; G01N 33/6893; G01N 2333/521; G01N 2333/988; G01N 2800/14; G01N 2800/7028; G01N 2800/7095; Y02A 90/10; A61P 1/04

See application file for complete search history.

(56) References Cited

U.S. PATENT DOCUMENTS

| | | |
|---|---|---|
| 4,735,214 A | 4/1988 | Berman |
| 5,738,110 A | 4/1998 | Beal et al. |
| 5,947,118 A | 9/1999 | Hochrainer |
| 6,475,145 B1 | 11/2002 | Baylor |
| 7,037,275 B1 | 5/2006 | Marshall et al. |
| 7,295,226 B1 | 11/2007 | Meron |
| 2006/0073561 A1 | 4/2006 | Rosen et al. |

(Continued)

FOREIGN PATENT DOCUMENTS

GB 1000078 A 8/1985

OTHER PUBLICATIONS

Roth et al., A comparison of a string test-PCR assay and a stool antigen immunoassay (HpSA) for Helicobacter, 2001, 95, 398-399 pylori screening in Peru (Year: 2001).*

Straumann et al., "Idiopathic eosinophilic esophagitis is associated with a T(H)2-type allergic inflammatory response", J. Allergy Clin. Immunol., 2001, vol. 108, pp. 954-961.

Thibeault et al., "Gene expression changes of inflammatory mediators in posterior laryngitis due to laryngopharyngeal reflux and evolution with PP! treatment: a preliminary study", Laryngoscope, 2007, vol. 117, pp. 2050-2056.

(Continued)

*Primary Examiner* — Narayan K Bhat
(74) *Attorney, Agent, or Firm* — Polsinelli PC

(57) ABSTRACT

In some embodiment, the present invention is directed to a device for obtaining samples from a subject. In other embodiments, methods and devices of the present invention allow the evaluation of conditions of the gastrointestinal tract of a subject. Measurements may be utilized, for example, to diagnose a disease of the esophagus, to monitor inflammation of the esophagus, or to access the treatment of a disease of the esophagus. In one embodiment, the invention comprises a method for measuring esophageal inflammation comprising deploying a device into the esophagus of a subject, removing the device after a predetermined period of time, analyzing the device for a diagnostic indicator of esophageal inflammation and evaluating the diagnostic indicator to diagnose esophageal inflammation.

20 Claims, 17 Drawing Sheets

(56) References Cited

U.S. PATENT DOCUMENTS

| | | |
|---|---|---|
| 2006/0231110 A1 | 10/2006 | Mintchev |
| 2007/0021360 A1 | 1/2007 | Nyce et al. |
| 2007/0161851 A1 | 7/2007 | Takizawa |
| 2007/0238942 A1 | 10/2007 | Baylor |
| 2009/0286237 A1 | 11/2009 | Fitzgerald |
| 2010/0300922 A1 | 12/2010 | Gilad |
| 2011/0031150 A1 | 2/2011 | Trigg |
| 2012/0226189 A1 | 9/2012 | Fitzgerald |

OTHER PUBLICATIONS

Thomas et al., "Use of the enterotest duodenal capsule in the diagnosis of giardiasis. A preliminary study", S. Afr. Med J., 1974, vol. 48, pp. 2219-2220.
Walsh et al., "Allergic esophagitis in children: a clinicopathological entity", Am. J. Surg. Pathol., 1999, vol. 23, pp. 390-396.
Yoshida et al., "Interleukin-8 expression in the esophageal mucosa of patients with gastroesophageal reflux disease", Scand. J. Gastroenterol., 2004, vol. 39, pp. 816-822.
Yu et al., "Intestinal epithelial CD23 mediates enhanced antigen transport in allergy: evidence for novel splice forms", Am. J. Physiol. Gastrointest. liver Physiol., 2003, vol. 285, pp. 0223-0234.
Ackerman et al., "Chapter 2: Human eosinophil lysophospholipase (charcot-leyden crystal proten): molecular cloning, expression, and potential functions in asthma", In: Eosinophils in Allergy and Inflammation, Gleich and Kay (Eds.) Marcel Dekker, NY, 1994, pp. 21-54.
Ackerman et al., "Charcot-Leyden crystal protein (galectin-10) is not a dual function galectin with lysophospholipase activity but binds a lysophospholipase inhibitor in a novel structural fashion", J. Biol. Chem., Apr. 2002, vol. 277, No. 17 pp. 14859-14868.
Ackerman et al., "The human eosinophil Charcot-Leyden crystal protein: biochemical characteristics and measurement by radioimmunoassay", J Immunol., Nov. 1980, vol. 125, No. 5, pp. 2118-2126.
Ackerman et al., "Eosinophilia and elevated serum levels of eosinophil major basic protein and Charcot-Leyden crystal protein (lysophospholipase) after treatment of patients with Bancroft's filariasis", J. Immunol., Sep. 1981, vol. 127, No. 3, pp. 1093-1098.
Ackerman et al., "Eosinophil degranulation. An immunologic determinant in the pathogenesis of the Mazzotti reaction in human onchocerciasis", J. Immunol., May 1990, vol. 144, No. 10, pp. 3961-3969.
Ackerman et al., "Molecular cloning and characterization of human eosinophil Charcot-Leyden crystal protein (lysophospholipase). Similarities to IgE binding proteins and the S-type animal lectin superfamily", J. Immunol., Jan. 1993, vol. 150, No. 2, pp. 456-468.
Arora et al., "Eosinophilic esophagitis: asthma of the esophagus?", Clin. Gastrointest. Nutr., 2004, vol. 2, pp. 523-530.
Bevilacqua et al., "Food allergens are protected from degradation during CD23-mediated transepithelial transport", Int. Arch. Allergy Immunol., 2004, vol. 135, pp. 108-116.
Blanchard et al., "Eosinophilic esophagitis: pathogenesis, genetics, and therapy", J. Allergy Clin. Immunol., 2006, vol. 118, pp. 1054-1059.
Blanchard et al., "Eotaxin-3 and a uniquely conserved gene-expression profile in eosinophilic esophagitis", J Clin. Invest., 2006, vol. 116, pp. 536-547.
Foroughi et al., "Clinical management of eosinophilic gastrointestinal disorders", Curr. Allergy Asthma. Rep., 2005, vol. 5, pp. 259-261.
Fox et al., "Eosinophilic esophagitis: it's not just kid's stuff", Gastrointest. Endosc., 2002, vol. 56, pp. 260-270.
Furuta et al., "Eosinophils alter colonic epithelial barrier function: role for major basic protein", J. Physiol. Gastrointest. liver Physiol., 2005, vol. 289, pp. 0890-0897.
Furuta et al., "Eosinophilic esophagitis in children and adults: a systematic review and consensus recommendations for diagnosis and treatment", Gastroenterology, 2007, vol. 133, pp. 1342-1363.
Furuta et al., "Hypoxia-inducible factor I-dependent induction of intestinal trefoil factor protects barrier function during hypoxia", J. Exp. Med., 2001, vol. 193, pp. 1027-1034.
Furuta et al., "Emerging questions regarding eosinophil's role in the esophago-gastrointestinal tract", Opin. Gastroenterol., 2006, vol. 22, pp. 658-663.
Furuta et al., "Parallel induction of epithelial surface-associated chemokine and proteoglycan by cellular hypoxia: implications for neutrophil activation", J Leukoc., 2000, vol. 68, pp. 251-259.
Genta et al., "The twentieth eosinophil", Adv. Anat. Pathol., 2007, vol. 14, pp. 340-343.
Gomes et al., "Eosinophil-fibroblast interactions induce fibroblast IL-6 secretion and extracellular matrix gene expression: implications in fibrogenesis", J Allergy Clin. Immunol., 2005, vol. 116, pp. 796-804.
Gonsalves et al., "Histopathologic variability and endoscopic correlates in adults with eosinophilic esophagitis", Gastrointest. Endosc., 2006, vol. 64, pp. 313-319.
Gowan et al., "Application of meso scale technology for the measurement of phosphoproteins in human tumor xenografts", Assay Drug. Dev. Technol., 2007, vol. 5, pp. 391-401.
Gracey et al., "Use of a simple duodenal capsule to study upper intestinal microflora", Arch. Dis. Child, 1977, vol. 52, pp. 74-76.
Gupta et al., "Cysteinyl leukotriene levels in esophageal mucosa] biopsies of children with eosinophilic inflammation: are they all the same?" Am. J Gastroenterol., 2006, vol. 101, pp. 1125-1128.
Gupta et al., "Cytokine expression in normal and inflamed esophageal mucosa: a study into the pathogenesis of allergic eosinophilic esophagitis", J. Pediatr. Gastroenterol. Nutr., 2006, vol. 42, pp. 22-26.
Gupta et al., "Eosinophilic esophagitis", Ear Nose Throat J., 2005, vol. 84, pp. 632-633.
Hogan et al., "Eosinophil Function in Eosinophil-associated Gastrointestinal Disorders", Curr. Allergy Asthma. Rep., 2006, vol. 6, pp. 65-71.
Isomoto et al., "Enhanced expression of interleukin-8 and activation of nuclear factor kappa-B in endoscopy-negative gastroesophageal reflux disease", Am. J. Gastroenterol., 99:589-97, 2004.
Kagalwalla et al., "Effect of six-food elimination diet on clinical and histologic outcomes in eosinophilic esophagitis", Clin. Gastroenterol. Hepatol., 2006, vol. 4, pp. 097-102.
Karhausen et al., "Epithelial hypoxia-inducible factor-I is protective in murine experimental colitis", J. Clin. Invest., 2004, vol. 114, pp. 1098-1106.
Kirsch et al., "Activated mucosa! mast cells differentiate eosinophilic (allergic) esophagitis from gastroesophageal reflux disease", J. Pediatr. Gastroenterol. Nutr., 2007, vol. 44, pp. 20-26.
Konikoff et al., "Potential of blood eosinophils, eosinophil-derived neurotoxin, and eotaxin-3 as biomarkers of eosinophilic esophagitis", Clin. Gastroenterol. Hepatol., 2006, vol. 4, pp. 1328-1336.
Li et al., "Transcytosis of IgE-antigen complexes by CD23a in human intestinal epithelial cells and its role in food allergy", Gastroenterology, 2006, vol. 131, pp. 47-58.
Liacouras et al., "Eosinophilic esophagitis: a 10-year experience in 381 children", Clin. Gastroenterol. Hepatol., 2005, vol. 3, pp. 1198-1206.
Mekjavic et al., "Determination of esophageal probe insertion length based on standing and sitting height", J Appl. Physiol., 1990, vol. 69, pp. 376-379.
Mishra et al., "An etiological role for aeroallergens and eosinophils in experimental esophagitis", J Clin. Invest., 2001, vol. 107, pp. 83-90.
Mishra et al., "Critical role for adaptive T cell immunity in experimental eosinophilic esophagitis in mice", J. leukoc. Biol., 2007, vol. 81, pp. 916-924.
Mishra et al., "IL-5 promotes eosinophil trafficking to the esophagus", J. Immunol., 2002, vol. 168, pp. 2464-2469.
Mishra et al., "Peyer's patch eiosinophils: identification, characterization, and regulation by mucosal allergen exposure, Interleukin-5, and eotaxin", Blood, 2000, vol. 96, pp. 1538-1544.
Montagnac et al., "Differential role for CD23 splice forms in apical to basolateral transcytosis of IgE/allergen complexes", Traffic, 2005, vol. 6, pp. 230-242.

(56) References Cited

OTHER PUBLICATIONS

Montagnac et al., "Intracellular trafficking of CD23: differential regulation in humans and mice by both extracellular and Intracellular exons", J. Immunol., 2005, vol. 174, pp. 5562-5572.

Oh et al., "Reduction of interleukin 8 gene expression in reflux esophagitis and Barrett's esophagus with antireflux surgery", Arch. Surg., 2007, vol. 142, pp. 554-560.

Plager et al. "A novel and highly divergent homolog of human eosinophil granule major basic protein", J. Biol. Chem., 1999, vol. 274, pp. 14464-14473.

Savidge et al., "Enteric glia regulate intestinal barrier function and inflammation via release of S-nitrosoglutathione", Gastroenterology, 2007, vol. 132, pp. 1344-1358.

Spergel, "Eosinophilic oesophagitis and pollen", Clin. Exp. Allergy, 2005, vol. 35, pp. 1421-1422.

Spergel et al., "The use of skin prick tests and patch tests to identify causative foods in eosinophilic esophagitis", J. Allergy Clin. Immunol., 2002, vol. 109, pp. 363-368.

Spergel et al., "Treatment of eosinophilic esophagi tis with specific food elimination diet directed by a combination of skin prick and patch tests", Ann. Allergy Asthma Immunol., 2005, vol. 95, pp. 336-343.

Spergel, "Eosinophilic esophagitis in adults and children: evidence for a food allergy component in many patients", Curr. Opin. Allergy Clin. Immunol., 2007, vol. 7, pp. 274-278.

Stein et al., "Anti-IL-5 (mepolizumab) therapy for eosinophilic esophagitis", J. Allery Clin. Immunol., 2006, vol. 118, pp. 1312-1319.

Straumann et al., "Cytokine expression in healthy and inflamed mucosa: probing the role of eosinophils in the digestive tract", Injlamm. Bowel Dis., 2005, vol. 11, 720-726.

Straumann et al., "Eosinophilic esophagitis: red on microscopy, white on endoscopy", Digestion, 2004, vol. 70, pp. 109-116.

* cited by examiner

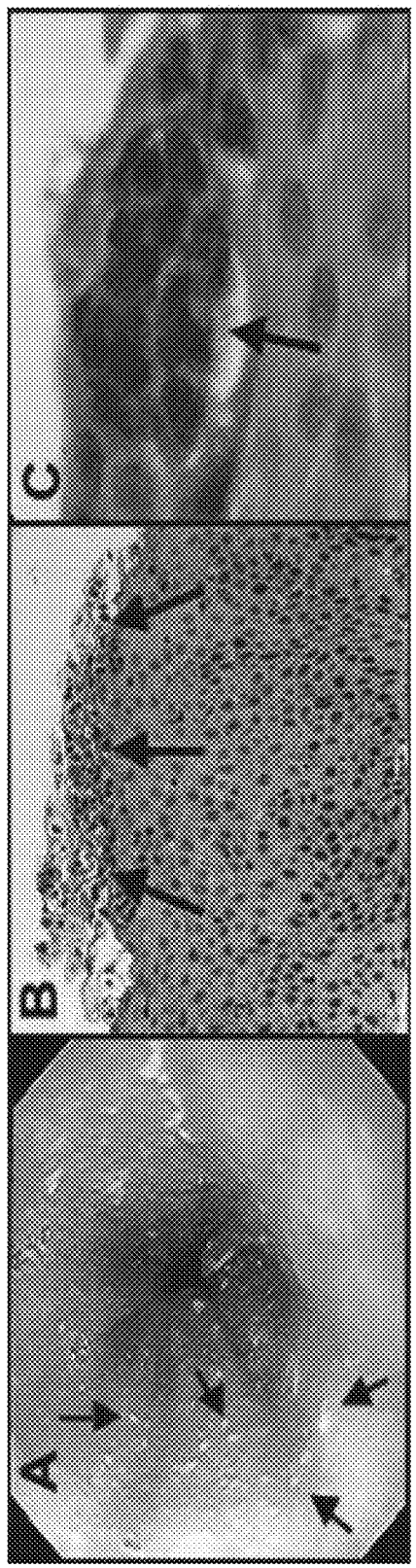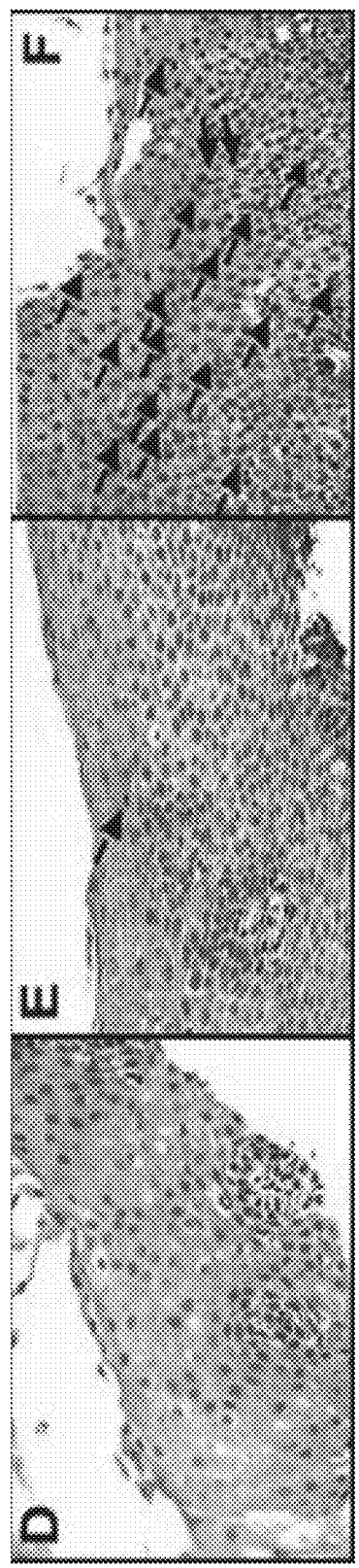

MINIMALLY-INVASIVE MEASUREMENT OF ESOPHAGEAL INFLAMMATION

RELATED APPLICATIONS

This application is a continuation of U.S. application Ser. No. 15/964,839 filed Apr. 27, 2018 which is allowed, which is a continuation of U.S. application Ser. No. 15/158,351 filed May 18, 2016, now U.S. Pat. No. 9,980,634, which is a continuation of U.S. application Ser. No. 14/136,811 filed Dec. 20, 2013, now U.S. Pat. No. 9,372,186, which is a continuation of U.S. application Ser. No. 12/741,549 filed May 5, 2010, now U.S. Pat. No. 8,637,239, which is a 371 National Phase application under 35 U.S.C. § 371 of International Application No. PCT/US2008/082482 filed Nov. 5, 2008, which claims the benefit of U.S. Provisional Patent Application No. 60/985,386 filed Nov. 5, 2007. These applications are incorporated herein by reference in their entirety for all purposes.

GOVERNMENT FUNDING

This invention was made with government support under grant numbers AI079925 and DK100303 awarded by National Institutes of Health and grant number FD-O-04086 awarded by Food and Drug Administration. The government has certain rights in the invention.

FIELD

The present invention relates generally to the field of medicine. In certain embodiments, the instant invention relates to devices and methods for diagnosing and monitoring conditions of the gastrointestinal tract in a subject.

BACKGROUND

Making the diagnosis of many inflammatory conditions of the gastrointestinal tract such as severe gastroesophageal reflux disease (GERD), eosinophilic gastroenteritis (EGE), food allergic enteropathy (FAE), and inflammatory bowel disease (IBD) is often difficult. Serologic and radiographic assessments are not diagnostic for any of these conditions. In the instance of food allergic disorders, skin prick testing and RAST analysis are the only non-invasive tests available. In addition, these tests are beneficial only in identifying IgE mediated reactions and are not useful for cell-mediated reactions. In other instances, non-invasive access to the gastrointestinal (GI) tract is only available through radiographic or stool analysis and again these do not provide definitive diagnostic information for these disorders.

Ultimately, endoscopic analysis is required to obtain mucosal sampling for diagnosis and to develop a treatment plan. Affected tissue sections are characterized by infiltration of polymorphonuclear leukocytes and eosinophils into the diseased sites. For some diseases, such as Crohn's disease, histopathological features are clear and characterized by the finding of chronic ileal inflammation with non-caseating mucosal granulomas. For other diseases, such as eosinophilic gastroenteritis and food allergic disorders, the exact histological features are not as certain and a degree of overlap with other conditions exists.

Methods to study esophageal diseases are limited to in vitro models, a few animal models and human studies of esophageal biopsies. Other, "minimally-invasive" esophageal studies can measure the amount of acid (pH monitor), non-acid (impedance monitor), and bile (Bilitec monitor) in the esophageal lumen. These later tests require placement of an inert probe (approximately 3 mm diameter) through the nose and into the distal esophagus for overnight monitoring. Another test of esophageal inflammation involves swallowing a capsule with a camera that can take pictures of the esophagus. Finally, esophageal function can be measured by placing probes into the esophagus for a pressure and waveform measurements (manometry/motility monitors).

U.S. Pat. No. 6,475,145 discloses a method utilizing a retrievable and ingestible radioactive capsule swallowed by a subject and held in place by means of a cord for diagnosis of GERD and acid-reflux. The radioactive capsule is degraded below pH4 so the measure is a radioactive release. The cord provides a means for retrieving the capsule.

U.S. Pat. No. 5,738,110 describes a device for the diagnosis of certain gastrointestinal pathogens. This device comprises a gelatin capsule which contains a drag material which has thin sample cloth embedded therein, which is attached to a string. The patient holds the string and swallows the capsule, allowing the sample cloth to come into contact with the small intestine. After a period of time, the sampling cloth and the drag material are recovered for testing.

To date, no method has been used to quantify the inflammatory contents of the esophageal lumen. Analogous to bronchial lavage in pulmonary diseases, stool collections in intestinal diseases and urinalysis in renal diseases, measurement of esophageal contents allows a direct definition and measurement of inflammatory mediators associated with esophageal diseases such as GERD and EE. A safe, "minimally invasive" alternative to endoscopy with biopsy to assess esophageal inflammation is therefore needed.

SUMMARY

The methods and apparatus of the present invention allow the evaluation of inflammation of the esophagus, by example, for diagnosis of disease of and assessment of treatment for a disease of the esophagus. In one embodiment, the invention comprises a method for measuring esophageal inflammation comprising deploying a device into the esophagus of a subject, removing the device after a predetermined period of time, analyzing the device for a diagnostic indicator of esophageal inflammation and evaluating the diagnostic indicator to diagnose esophageal inflammation.

In another embodiment, the present invention provides a method for diagnosing a disease of the esophagus comprising deploying a device into the esophagus of a subject, removing the device after a predetermined period of time, analyzing the device for a diagnostic indicator of a disease of the esophagus and evaluating the diagnostic indicator to diagnose a disease of the esophagus.

In other embodiments, the invention comprises a method for assessing a treatment of a disease of the esophagus comprising deploying a device into the esophagus of a subject, removing the device after a predetermined period of time, analyzing the device for a diagnostic indicator of a disease of the esophagus and evaluating the diagnostic indicator to assess the treatment of a disease of the esophagus.

The current invention may be used to measure any cause of inflammation of the esophagus. This measurement may be utilized, for example, to diagnose a disease of the esophagus, to monitor inflammation of the esophagus, or to access the treatment of a disease of the esophagus. The disease of the esophagus may comprise inflammation of the esophagus.

For example, the current invention may be used to assess and diagnose gastroesophageal reflux disease (GERD) or complications associated with GERD such as Barrett's esophagus or cancer. In another non-limiting embodiment, the disease may be Eosinophilic Esophagitis (EE).

The device may be any apparatus which allows the capture of the inflammatory mediators and other cells of the esophagus. In one embodiment, the device comprises a pharmaceutical capsule having an opening, a drag material within the capsule, and a line embedded in the drag material that runs through the opening of the capsule. The pharmaceutical capsule may be dissolvable or it may pass through the subject's system. In another embodiment, the capsule may be comprised of two parts, a base and a cap, and the opening of the capsule may be a perforated opening. The drag material may be constructed of various materials. In some embodiments, the drag material is malleable. The line may be of various lengths and may be made of various materials to be more or less abrasive and more or less absorptive. In a particular embodiment, the line comprises two components, a string and a sampling cloth. The string component may be referred to as the proximal segment, whereas the sampling cloth may be referred to as the distal segment. In some embodiments, after deployment of the string, the proximal segment is located in the esophagus of the subject. The string may be made of, for example, an absorbent, mesh, or textured fiber. In one embodiment, the string and sampling cloth are constructed of the same material. In some embodiments, a portion of the string may be pulled out of the capsule prior to swallowing the capsule and the end of the string may be attached to the cheek. After the predetermined period of time, the string may be removed from the esophagus.

In another embodiment, the device further comprises a capture agent for one or more diagnostic indicators. These capture agents may be located on the line. In a particular embodiment, the capture agents may be focused on the proximal segment of the line. The capture agent may be any agent that binds an analyte through an interaction that is sufficient to permit the agent to bind and concentrate the analyte from a homogeneous mixture of different analytes. The binding interaction may be mediated by an affinity region of the capture agent. Representative capture agents include antibodies, and more specifically monoclonal antibodies. Further non-limiting examples include eosinophil granule protein antibodies.

The predetermined period of time may be various lengths of time. For example, the predetermined time may be between 15 minutes and 12 hours. In some embodiments, the predetermined period of time may be 1, 2, 3, 4, 5, 6, 7, 8, 9, 10, 11, 12, 18, 24 or more hours, or any increment thereof. In one embodiment, the predetermined period of time is 15 minutes. In another embodiment, the predetermined period of time is 1 hour. In a further particular embodiment, the predetermined period of time is 12 hours.

Following removal of the device from the esophagus, the device is analyzed for diagnostic indicators. The line may be made of various materials to be more or less abrasive and more or less absorptive. In some embodiments, the indicator is adsorbed in the device. In other embodiments, the indicator binds to the outside of the device. In yet a further embodiment, liquid may adhere to the device. In yet a further embodiment, secretions may adhere to the device. As noted above, in one embodiment a capture agent for one or more diagnostic indicators may be present on the device, wherein the diagnostic indicator may bind to the capture agent. Secretions and cells can be examined by a number of different techniques known in the art. The presence of inflammatory proteins, RNA or cells can be analyzed within the contents removed from the string.

The device is analyzed for a diagnostic indicator of esophageal inflammation. In some embodiments, the device is analyzed for the presence of one or more diagnostic indicators. In other embodiments, the device is analyzed for the level of one or more diagnostic indicators. Analysis may be performed by a number of methods, including but not limited to ELISA, cytology, mass spectrometry, gas chromatography, Western Blot, Mesoscale, Licor, RNA and DNA extraction, immunohistochemical analysis, and microbial culture and staining.

The diagnostic indicator may be any factor that indicates the presence or severity of inflammation of the esophagus. In some aspects, the diagnostic indicator may be an eosinophil granule protein, including major basic protein (MBP), an eosinophil cationic protein (ECP), an eosinophil peroxidase (EPO), or an eosinophil-derived neurotoxin (EDN). In some embodiments, the diagnostic indicator is a cytokine or chemokine, such as eotaxin. In another embodiment, the diagnostic indicator is a cellular infiltrate or pH. In yet another embodiment, the diagnostic indicator is a marker of an allergic response, such as IgE, tryptase, receptor molecules (for example, FcRI or CD23) or an allergen. Other inflammatory markers that may be examined may include, for example, arachidonic acid products and neurotransmitters such as substance P and bradykinin. Other diagnostic indicators include peripheral and plasma eosinophil counts, mast cells, including leukotrienes. In other aspects, diagnostic indicator comprises one, two or more markers.

In some embodiments, the eosinophil granule protein may be induced. In a particular embodiment, the eosinophil granule protein is IL-5 induced. In further embodiments, the IL-5 induced eosinophil granule protein is EPO, MBP1, or CLC/Gal-10.

The diagnostic markers are evaluated to diagnose a disease of the esophagus. Evaluation may include assessment for the presence or absence of an indicator that allows for diagnosis of a disease. For example, if a sample shows evidence of an inflammatory reaction, this may indicate the presence of eosinophilic esophagitis. Alternatively, the level of an indicator may be evaluated to either diagnosis or evaluate the level of severity of a disease. For instance, the evidence may be increased levels of eosinophil granule proteins that may indicate the presence of EE. In other non-limiting embodiments, increases in specific cytokines, such as IL-6, indicates the presence of GERD. In a particular embodiment, the diagnostic indicator for GERD may be IL-8 mRNA or IL-8 protein.

In one embodiment, the invention provides a method for measuring esophageal inflammation comprising deploying a device into the esophagus of a subject, removing the device after a predetermined period of time, analyzing the device for a diagnostic indicator of esophageal inflammation, and evaluating the diagnostic indicator to diagnose esophageal inflammation. In a further embodiment, the method may further comprise quantifying the diagnostic indicator. The quantification may be performed by any method known to those of skill in the art. In a particular embodiment, the quantification is performed by ELISA. In a further embodiment, the quantification is performed by Mesoscale.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) The extended Enterotest™ string is shown with the Gelatin capsule at the distal end (bottom left arrow). The proximal end that gets taped to the patient's cheek is thinner (top right, arrow). (FIG. 2B) Segment of an Enterotest™ string from a normal subject is shown with pH indicators (and indicator stick), demonstrating the location of the sections of string that were in the esophagus (alkaline pH, blue-green) and stomach (acidic pH, orange). Only the colored portions of the string were marked for pH using the indicator stick.

FIGS. 6A-F. (FIG. 6A) Endoscopic view of the esophagus of an EE patient, showing multiple eosinophil microabscesses (white dots, arrows) painting the inflamed epithelial surface. (FIGS. 6B-C). H&E sections showing one of these eosinophil microabscess erupting through the epithelium into the lumen 0, and one just beneath the surface (FIG. 6C arrow). (FIGS. 6D-F). Three biopsies from the same EE patient showing normal-appearing squamous epithelium (FIG. 6D), a site with hyperplastic epithelium with 1 eosinophil/HPF (FIG. 6E arrow), and a site with hyperplastic epithelium with >15 eosinophils/HPF (FIG. 6F arrows), emphasizing the discontinuity of esophageal eosinophilic inflammation in EE.

(FIG. 12A) H&E section of biopsy from patient with GERD showing evidence of mild eosinophilic inflammation (arrow) and basal zone hyperplasia consistent with GERD. (FIG. 12B) The Enterotest was performed in this patient and removed after 12 hours. The string was cut into oral, esophagus (proximal and distal), stomach and duodenum segments based on position (length) and pH indicator measurements. Protein secretions were eluted from the string segments, IL-8 protein levels measured using the Quantitative Mesoscale assay, and results expressed as pg IL-8/ml/cm of the Enterotest string samples.

DETAILED DESCRIPTION

Figure 1:
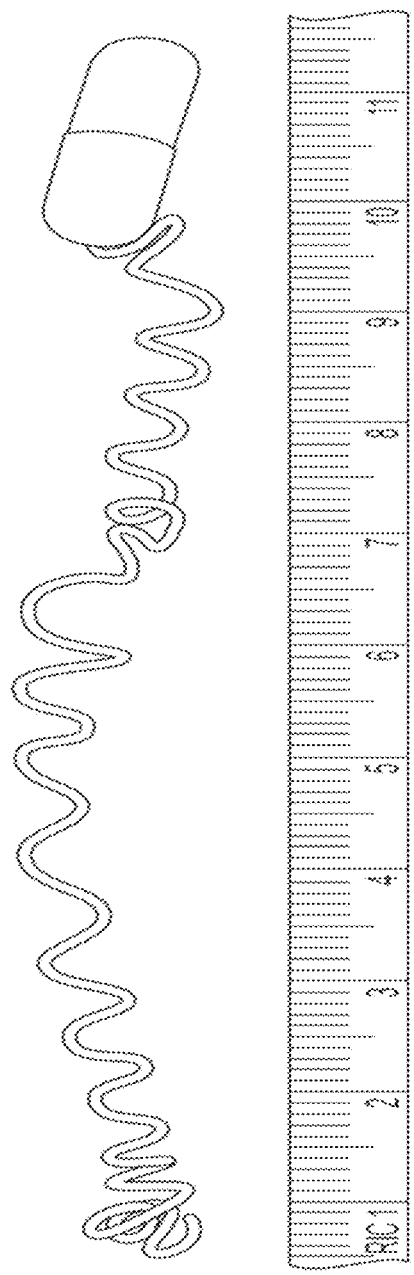
FIG. 1. Enterotest™ string test—the 90 cm nylon string is shown partially unraveled from the gelatin capsule.

The methods and apparatus of the present invention allow the evaluation of inflammation of the esophagus. In one embodiment, the invention comprises a method for measuring esophageal inflammation comprising deploying a device into the esophagus of a subject, removing the device after a predetermined period of time, analyzing the device for a diagnostic indicator of esophageal inflammation and evaluating the diagnostic indicator to diagnose esophageal inflammation.

This method provides a minimally invasive method for assessing and diagnosing a disease of the esophagus. The methods of the present invention may be used, for example, in assessing inflammation of the esophagus such as gastroesophageal reflux disease (GERD) and Eosinophilic Esophagitis (EE). For a long period of time, eosinophilic inflammation of the esophagus was felt to be almost exclusively due to GERD. Clinicopathological analysis has now demonstrated that esophageal eosinophilia can also be due to EE, which is a disease typically having an allergic etiology. EE has emerged as a distinct type of esophagitis, however the distinction between EE and GERD is frequently difficult to identify. For example, the two diseases can be difficult to differentiate by conventional methods, as GERD and EE can have similar presentations and upper gastrointestinal series are insensitive tests for the diagnosis of GERD. EE is characterized both by its association with food allergens and also by the large number of eosinophils that are usually present in the esophagus of diagnosed patients. However, in some biopsies the eosinophil count falls within a borderline range and inflammation can be inconsistent. Eosinophils contain a number of cytokines, chemokines, and granular proteins. These biologically active mediators are released upon activation to participate in the inflammatory cascade. The method of the current invention allows for a minimally-invasive alternative for diagnosis of these and other diseases.

1. Devices

The device may be any apparatus which allows the capture of the inflammatory mediators and other cells of the esophagus. In a particular embodiment, the device of the current invention comprises a pharmaceutical capsule having an opening, a drag material within the capsule, and a line embedded in the drag material and running through the opening of the capsule. The phrase "pharmaceutical" refers to molecular entities and compositions that do not produce an adverse, allergic, or other untoward reaction when administered to an animal, or human, as appropriate. The pharmaceutical capsule may be dissolvable or it may pass through the subject's system. In some aspects, the opening of the capsule may be a perforated opening. In another embodiment, the capsule may be comprised of two parts, a base and a cap. The drag material may be constructed of various materials. In some embodiments, the drag material is malleable. The drag material may also be eliminated. The line may be of various lengths and may be made of various materials to be more or less abrasive and more or less absorptive. In a particular embodiment, the line comprises two components, a string and a sampling cloth. The string component may be referred to as the proximal segment, whereas the sampling cloth may be referred to as the distal segment. The string may be made of, for example, an absorbent fiber, mesh, or a textured fiber.

In one embodiment, the string and sampling cloth are constructed of the same material. The line and the sampling cloth may be of various proportions. In some embodiments, a portion of the string may be pulled out of the capsule prior to the subject swallowing the capsule, and the end of the string may be attached to the cheek. After the predetermined period of time, the string may be removed from the esophagus.

U.S. Pat. No. 6,475,145, incorporated by reference, discloses a retrievable and ingestible radioactive capsule swallowed by a subject and held in place by means of a cord for diagnosis of GERD and acid-reflux. The radioactive capsule is degraded below pH4 so the measure is a radioactive release. The cord provides a means for retrieving the capsule. U.S. Pat. No. 5,738,110, incorporated by reference, describes a device for the diagnosis of certain gastrointestinal pathogens. This device comprises a gelatin capsule which contains a drag material which has thin sample cloth embedded therein, which is attached to a string. The patient holds the string and swallows the capsule, allowing the sample cloth to come into contact with the stomach. Both of these devices may be adapted for use in the present invention.

In another embodiment, the device further comprises a capture agent for one or more diagnostic indicators. These capture agents may be located on the line. In a particular embodiment, the capture agents may be localized on the proximal segment of the line. The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include antibodies, and more specifically monoclonal antibodies. Further non-limiting examples include eosinophil granule protein antibodies. The phrase "surface-bound capture agent" refers to an agent that is immobilized on a surface of a solid substrate, where the substrate can have a variety of configurations, e.g., a string.

The predetermined period of time may be various lengths of time. For example, the predetermined time may be between 15 minutes and 12 hours. In some embodiments, the predetermined period of time may be 1, 2, 3, 4, 5, 6, 7, 8, 9, 10, 11, 12, 18, 24 or more hours, or any increment thereof. In one embodiment, the predetermined period of time is 15 minutes. In another embodiment, the predetermined period of time is 1 hour. In a further particular embodiment, the predetermined period of time is 12 hours.

a. The Esophageal String Test (EST)

Figure 2A:
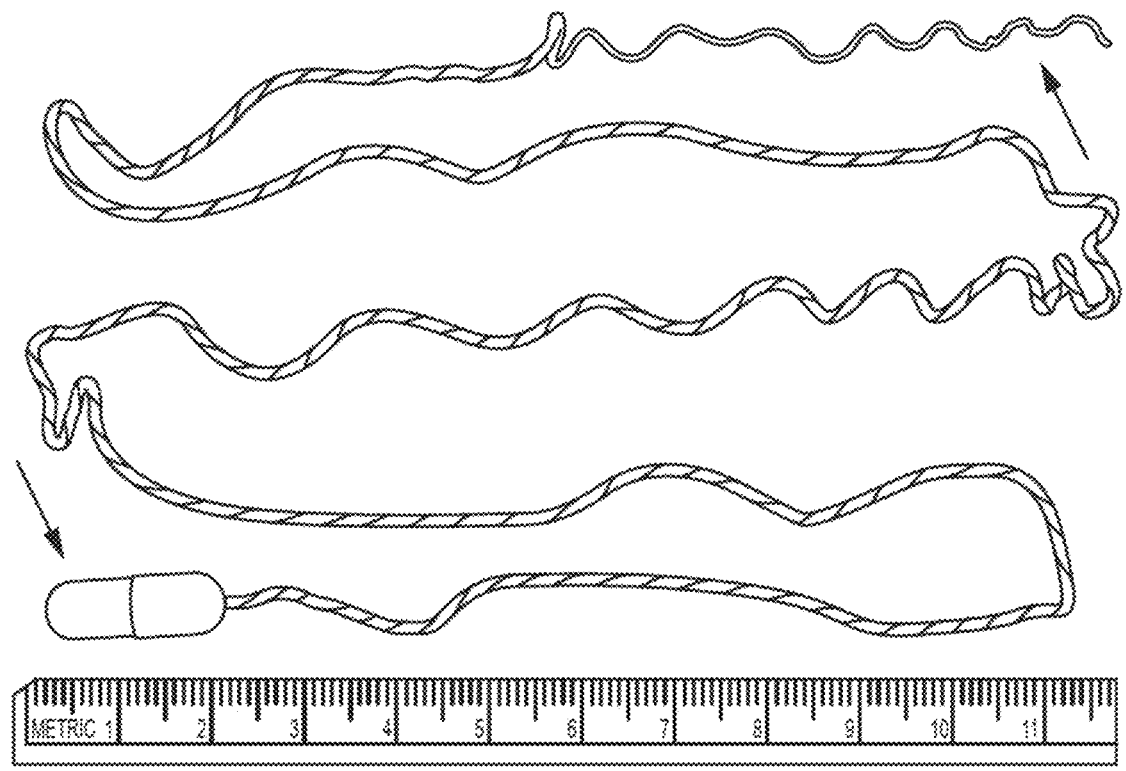
FIGS. 2A-B. Enterotest™ string test.
Figure 2B:
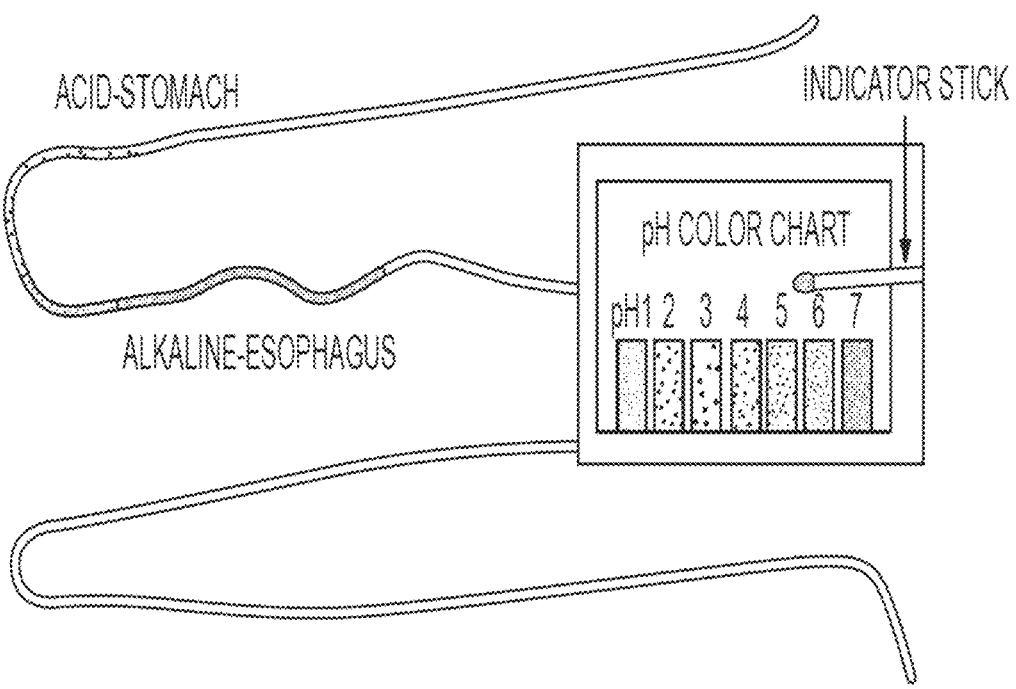

The Enterotest™ (FIG. 2) (HDC Corporation) was developed as a minimally invasive method to assess for small intestinal parasites, e.g., *Giardia lamblia* (Gracey et al., 1977; Thomas et al., 1974). After the capsule is swallowed, the distal end of the nylon fiber string (nearest the gelatin capsule) (FIG. 2A-bottom arrow) resides in the lumen of the small intestine, and adherent mucous, secretions and parasites (if present), adhere to the nylon string and upon stripping from the string, can be detected by light microscopy. The anatomical location of the string can be identified by the provided pH indicator that is touched to portions of the string to identify where boundaries between acid and alkaline sections of string and thus where the esophageal, gastric and small intestinal Enterotest™ sections resided (FIG. 2B). In the rare patients who are achlorhydric or who are on acid blockading medications, the standardized formula would be used in the placement of pH monitors to calculate esophageal length (Mekjavic I B, Rempel et al., 1990).

It is expected that the more proximal end of the string residing within the esophagus will capture inflammatory markers from esophageal secretions, as well as squamous epithelial and inflammatory cells, i.e. eosinophils, present in microabscesses (FIG. 6), thus allowing for a minimally invasive measurement of esophageal inflammatory disease and remission in EE. In the Esophageal String Test (EST), the thinner proximal end of the Enterotest™ string (FIG. 2—top arrow) is taped to the patient's cheek, and the capsule is swallowed, leaving a trail of string in its path through the esophagus and into the duodenum (FIG. 2—bottom arrow). Within a short period of time, the gelatin capsule dissolves and the end of the string is left free in the duodenum. The EST is left in place for between 15 minutes and 12 hours and is then removed for analysis as described below. Herein, evidence that the EST provides a sensitive and specific method for analyzing esophageal luminal markers of inflammation at the protein and mRNA levels is presented. The original Enterotest™ will be used without any modifications.

Endoscopic and histopathological representations relevant to this test are shown in FIG. 6. A significant percentage of patients with EE show evidence of superficial eosinophil-rich exudates as evidenced by the gross endoscopic view (FIG. 6A) (Sundaram et al. 2004) and corresponding histological section (FIG. 6B). Even if there is no gross evidence of exudation, intact and degranulating eosinophils and eosinophil microabscesses are routinely present along the superficial epithelial surface allowing for assessment of their secreted mediators (FIG. 6C) by the EST (Straumann et al., 2004; Walsh et al. 1999). Importantly, the 4-6 mucosal biopsies usually obtained for EE diagnosis capture only a small fraction (<0.01%) of the total surface area of the esophagus and may be highly variable in their findings. For example, histological sections from 3 biopsies of the same patient taken at different locations during the same endoscopy show: (1) normal appearing epithelium (FIG. 6D), (2) epithelium with minimal eosinophilic inflammation (<1 eosinophil/HPF) (FIG. 6E) and (3) a more distal site with the typical diagnostic appearance of EE with large numbers of eosinophils (>15/HPF) (FIG. 6F). This discontinuity in eosinophilic inflammation can be easily missed by biopsy, thus making the proposed EST, which would provide a more holistic measure of inflammation through the entire length of the esophageal lumen, a more complete and valuable assessment.

2. Analyzing the Device

Following removal of the device from the esophagus, the device is analyzed for a diagnostic indicator. As explained above, the line may be made of various materials to be more or less abrasive and more or less absorptive. In some embodiments, the indicator is adsorbed in the device. In another embodiment, the indicator binds to the outside of the device. In such embodiments, the collected indicators may be scraped off of the sampling cloth for analysis. In yet a further embodiment, secretions may adhere to the device. Secretions and cells can be examined by a number of different techniques known in the art. The presence of inflammatory proteins, RNA or cells can be analyzed within the contents removed from the string. As noted above, in one embodiment a capture agent for one or more diagnostic indicators may be present on the device, wherein the diagnostic indicator may bind to the capture agent. In some embodiments, the device is analyzed for the presence of one or more diagnostic indicators. In other embodiments, the device is analyzed for the level of one or more diagnostic indicators. Analysis may be performed by a number of methods, including but not limited to ELISA, cytology, mass spectrometry, gas chromatography, Western Blot, Mesoscale, Licor, RNA and DNA extraction, immunohistochemical analysis, and microbial culture and staining. Some of these methods, such as mesoscale and Licor, are recently described technologies and are described in, for example, Savidge et al. (2007) and Gowan et al. (2007). The other methods for analyzing the products are well known in the art, and are described in, for example, Sambrook et al. (2001) and Ausubel et al. (1994).

3. Diagnostic Indicators

The diagnostic indicator may be any factor that indicates the presence or severity of inflammation of the esophagus. The diagnostic indicator may be an eosinophil granule protein, a cytokine or chemokine, a cellular infiltrate, pH, or a marker of an allergic response. Other diagnostic indicators include peripheral and plasma eosinophil counts, mast cells, including leukotrienes. In other aspects, diagnostic indicator comprises one, two or more markers.

a. Esophageal Granule Protein

Eosinophil granule proteins include major basic protein (MBP), eosinophil cationic protein (ECP), eosinophil peroxidase (EPO), and eosinophil derived neurotoxin (EDN). These proteins are secreted on eosinophil stimulation and actively participate in the subsequent inflammatory response. Eosinophil granule proteins also include other biologically active products including bacterial permeabilizing protein (BPP) and anti-microbial proteins. Secretion and extracellular deposition of eosinophil granule proteins in tissues affected by inflammatory diseases suggests that MBP, ECP, EPO, and EDN may participate in the pathogenesis of the inflammatory process. Further evidence has demonstrated that the topical application of MBP is associated with tracheal smooth muscle contraction and ion secretion. It has been demonstrated that one of these proteins, in particular, MBP can stimulate the release of the inflammatory cytokine IL-8 from stromal cells within the gastrointestinal tract. In addition, the deposition of major basic protein has been found in inflamed tissues of patients affected with colitis and esophagitis.

b. Cytokines and Chemokines

Clinical relevance for many cytokines and chemokines have now been established. Cytokines include the interleukins (IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-32) and interferons. In particular, a diagnostic factor may be a Th2 cytokine (e.g., IL-4, IL-5, IL-13). Chemokines include, for example, the eosinophil-specific chemokines eotaxin-1, -2, -3.

c. Marker of an Allergic Response

A marker of an allergic response may also indicate the inflammation of and disease of the esophagus. An "allergic response" as used herein is a disorder in which the host's immune response to a particular antigen is unnecessary or disproportionate, resulting in pathology. Allergies arising from an allergic response include, but are not limited to, allergies to pollen, ragweed, shellfish, any food product, domestic animals, (e.g., cats and dogs), B-venom, and the like. A subset of allergic responses produce asthma. Allergic asthmatic responses are also included within the definition of the term "allergic response."

A marker of an allergic response may be, for example, immunoglobulin E (IgE), tryptase, receptors (FcRI, CD23) or an allergen. CD23 is a low-affinity receptor for IgE, expression of which is induced by cytokines associated with allergic responses. Other inflammatory markers that may be examined may include, for example, arachidonic acid products and neurotransmitters such as substance P and bradykinin.

4. Evaluation of Diagnostic Indicators

The diagnostic markers are evaluated to diagnose a disease of the esophagus. Evaluation may include the presence or absence of an indicator that allows for diagnosis of a disease. For example, if a sample shows evidence of an inflammatory reaction, this may indicate the presence of eosinophilic esophagitis. Alternatively, the level of an indicator may be evaluated to either diagnosis or evaluate the level of severity of a disease. For instance, the evidence may be increased levels of eosinophil granule proteins that may indicate the presence of EE. In other non-limiting embodiments, increases in specific cytokines, such as IL-6, indicates the presence of GERD. The diagnostic markers may also be evaluated to assess the treatment of a disease.

B. Diseases of the Esophagus

The present invention may be used to diagnose or assess treatment of a disease of the esophagus. The disease of the esophagus may be any disease that comprises inflammation of the esophagus.

1. Gastroesophageal Reflux

In certain aspects, the disease may be gastroesophageal reflux disease (GERD). GERD is defined as chronic symptoms or mucosal damage produced by the abnormal reflux in the esophagus. Symptoms may include heartburn, inflammation in the esophageal lining, strictures, dysphagia and chronic chest pain. Methods of diagnosis include barium swallow X-rays, esophageal manometry, 24-hour esophageal pH monitoring, and esophagogastroduodenoscopy. Treatments include food and lifestyle modifications, positional therapy, drug treatment and surgery. The current invention may be used to assess and diagnose GERD or complications associated with GERD such as Barrett's esophagus or cancer.

2. Eosinophilic Esophagitis

In another embodiment, the disease may be Eosinophilic esophagitis (EE). EE, an increasingly recognized eosinophilic gastrointestinal disease (EGID), accounts for .about. 50% of dysphagia and food impaction. It has been proposed that food allergy is the underlying etiology of EE. Recent translational studies show that skin prick tests (SPTs) are currently the best available tool to identify the triggering food allergens and >90% of patients respond to dietary interventions, thus supporting a role for humoral (IgE) and/or cell-mediated food allergy. In addition, esophageal mast cells are significantly increased in EE compared to normal controls and gastroesophageal reflux disease (GERD). Notably, of various dysregulated genes identified by DNA microarray studies, five mast cell genes were highly induced, including the high-affinity IgE receptor (FcεRI) and mast cell tryptase-α. However, the role of IgE-mediated mast cell (or basophil) responses in the esophageal inflammatory cascade in EE remains uncertain, as noted by the fact that RAST testing alone shows poor specificity for identifying offending foods. To date, no studies have prospectively examined the role of IgE in the esophageal microenvironment associated with EE.

EE is a disorder of the esophagus characterized by esophageal and/or upper gastrointestinal tract symptoms in association with esophageal mucosal biopsy specimens containing high amount of intraepithelial eosinophils within the esophageal squamous epithelium or deeper tissue levels and normal pH monitoring. EE affects males more than females, and the diagnosis is typically made in adults during the third and fourth decades of life, although it may be diagnosed at a later age. In children, the diagnosis is made after infancy and through adolescence with no recognized peak age of onset. Symptoms may include chest pain, heartburn, dysphagia, food impaction and a lack of responsiveness to acid reducing medications. Treatment of EE involves either corticosteroids or elemental diet and not surgery.

Standard of care for EE patients includes initial esophageal endoscopy with biopsy to determine the numbers of epithelial eosinophils (.ltoreq.15/hpf being diagnostic). Since consequences of chronic eosinophilic inflammation in EE can include esophageal remodeling with subsequent esophageal narrowing, trachealization and strictures, therapeutic efforts are typically devoted toward inducing clinical as well as histological remission. While overall relatively safe, esophageal endoscopy entails procedural risks, is expensive, time consuming and is limited to procuring a 3 mm sample.

To date, no serological, stool or non-invasive tests have provided durable results correlating histological evidence of disease progression or remission in EE. Presently, the state of esophageal inflammation in patients with EE can only be assessed with an invasive endoscopy. Although the cost-benefit ratio is unknown, repeated endoscopies with biopsies are the best test tool date to assess disease status and response to treatment.

To address this issue, an Esophageal String Test or EST, such as the Enterotest™ a string-based test first used for detection of Giardia infections, can be used in its native form to assess esophageal inflammation at both the protein and mRNA levels and may potentially be used to monitor disease activity. The EST may offer a minimally invasive method to assess the presence of inflammation associated with active disease.

a. Eosinophilic Esophagitis and Food Allergies

Food allergic diseases affect between 4-6% of children in the United States per year. During the last decade, an increasing number of children developed a new manifestation of food allergy termed eosinophilic esophagitis (EE) (Furuta et al., 2007). Several lines of evidence support a close relationship of EE with food allergic diseases. First, skin prick testing (SPT), a reliable indicator of IgE-mediated food reactions, correlates consistently with esophageal inflammation in EE (Spergel, 2007). Second, patients with EE often associate symptoms following the ingestion of specific foods. Furthermore, specific elimination of those foods and/or foods identified by SPTs leads to clinicopathological remission in EE (Spergel et al., 2002; Kagalwalla et al., 2006). Third, mucosal biopsies from patients with EE demonstrate significantly increased numbers of mucosal mast cells compared to those from patients with gastroesophageal reflux disease (GERD) or normal subjects, suggesting their participation in the pathogenesis of this disease (Kirsch et al., 2007) Finally, previous work suggests that patients with eosinophilic gastrointestinal diseases (EGIDs) and food allergy demonstrate increased expression of CD23 on intestinal epithelial cells and in stool samples (Li et al. 2006). While the precise role of CD23 in food allergic responses is not certain, recent studies suggest that the human CD23a isoform participates as a bidirectional transporter of both free IgE and IgE/antigen complexes, and can potentially deliver IgE and its bound allergen across intestinal epithelial cells to induce mast cell activation (Montagnac et al. 2005a; Montagnac et al., 2005b; Bevilacqua et al., 2004; Yu et al., 2003). Taken together, these observations provide strong evidence supporting a role of food allergic responses (including those mediated by IgE) in the pathogenesis of EE.

b. Diagnostic Criteria for Eosinophilic Esophagitis

The recent emergence of EE is emphasized by the fact that diagnostic criteria have only recently been established (Furuta et al., 2007). Clinically, EE is characterized by symptoms including abdominal pain, regurgitation, feeding intolerance, food impaction and dysphagia. Histologically, esophageal biopsies contain large numbers of intraepithelial eosinophils (.gtoreq.15 eosinophils/high power field), often with eosinophil microabscesses and luminal layering. These findings are unresponsive to acid blockade, e.g. proton pump inhibition, but do respond to elimination (or elemental) diets and corticosteroids. This disease does not affect the columnar epithelium of the stomach or small intestine. Thus, when a patient has persistent symptoms that are associated with esophageal epithelial eosinophilia and normal gastric and duodenal mucosa, and gastroesophageal reflux (GERD) and other causes of eosinophilia have been ruled out, the diagnosis of EE can be made with confidence. The importance of clear diagnostic criteria is emphasized by the fact that many patients are now receiving the diagnosis of EE based on histological findings alone, without proper investigations to exclude other causes of esophageal eosinophilia (Genta et al., 2007; Ngo et al., 2006).

c. Pathogenesis of Eosinophilic Esophagitis

Although a number of factors relate food allergic responses to EE, the exact mechanisms defining the pathogenesis of EE remain uncertain (Hogan and Rothenberg, 2006). Current paradigms of potential mechanisms underlying EE address several different pathways including, the role of IgE in EE (Foroughi and Prussin, 2005), identifying the mechanisms of squamous eosinophilia (Blanchard et al., 2006a), and defining whether the associated phenotype of patients is predominantly Th1 or Th2 (Straumann et al., 2001; Straumann et al., 2005). A few translational studies have addressed the participation of IgE-mediated immediate hypersensitivity responses in EE. Increased numbers of mast cells (Kirsch et al., 2007), CD23 expression on intestinal epithelial cells (Li et al., 2006), and historical evidence of other IgE-mediated allergic diseases (Spergel, 2005), provide circumstantial evidence supporting a role for IgE-mediated responses in EE. Alternatively, not all patients have elevated total or specific IgE, show evidence of atopic disease, or have increased mast cells in their esophageal tissue (Furuta et al., 2007). Typically, patients do not complain of immediate reactions associated with the ingestion of candidate foods, and do not present with systemic allergic symptoms involving other organs such as the lung or skin, although EE has been referred to by some as "asthma or eczema of the esophagus" (Arora and Yamazaki, 2004).

A recent translational study focused on one potential mechanism that drives eosinophils into the esophageal squamous epithelium (Blanchard et al., 2006a). A DNA microarray study showed that the eosinophil-specific chemoattractant eotaxin-3 (CCL26) was the most highly up-regulated gene in the squamous epithelium from biopsies of patients with EE compared to those with GERD and those with normal mucosa. In this report, studies using eotaxin receptor CCR3-deficient (knockout) mice confirmed that esophageal eosinophilia, in an IgE-dependent intranasal allergen model, was dependent on the presence of CCR3 for eosinophil recruitment to the esophagus. Finally, 32.1% of EE patients compared to 22.4% of non-EE matched subjects in this study had a single nucleotide polymorphism (SNP)+2,496 T→G in the eotaxin-3 gene that was associated with disease susceptibility. Thus, eotaxin-3 remains the only biomarker to date associated with EE. However, since only a limited percentage of patients possessed this eotaxin-3 SNP, it is likely that other relevant biomarkers will be identified.

Basic and clinical studies suggest that the preponderance of inflammatory responses associated with EE is of a Th2 phenotype. As demonstrated in murine models utilizing IL-5 and eotaxin-1 null mice, esophageal eosinophilia is dependent on IL-5 expression and partially dependent on eotaxin-1 (Mishra et al., 2001; Mishra et al., 2002). Histological staining of affected esophageal epithelium shows increased IL-5 staining (Straumann et al., 2001; Straumann et al., 2005) and a recent small clinical series showed that anti-IL-5 antibody leads to the resolution of clinical and histological findings in some EE patients (Stein et al., 2006). While food allergen-induced responses leading to over-expression of eotaxin-3 by the squamous epithelium in the esophagus is likely involved in the Th2 inflammatory cascade, the precise pathogenesis of esophageal eosinophilia in EE has yet to be established. To date, eotaxin-3 is the only potential biomarker that has been identified for EE.

d. Problems Associated with Care of Patients with EE

While treatments of EE have become well accepted in terms of the use of nutritional elimination diets (Kelly et al., 1995; Markowitz et al., 2003; Spergel et al., 2005), including elemental diets, and corticosteroid administration (Faubion et al., 1998; Liacouras et al., 1998), the precise treatment endpoints are much less clear (Furuta et al., 2007). For instance, some clinicians treat to resolve only symptoms, while others treat to induce both clinical and histological remission, i.e. treat to decrease numbers of esophageal eosinophils (Aceves et al., 2008). This decision is often shaped by the reluctance to have patients undergo repeated esophagogastroduodenoscopy (endoscopy) and biopsies, and by uncertainty about the natural history and incidence of long-term sequelae of chronic esophageal eosinophilia that include esophageal remodeling, subepithelial fibrosis and narrowing. Those who feel that chronic esophageal eosinophilia leads to esophageal fibrosis and stricture formation treat patients and perform repeat endoscopy with biopsy to insure that mucosal eosinophilia has resolved. Those who feel that chronic esophageal eosinophilia will not lead to esophageal strictures will treat with symptom relief as the only endpoint and not repeat endoscopy with biopsy. Thus, a significant number of EE patients who never undergo post-treatment sampling of their mucosa may continue to have mucosal disease that could possibly leave them vulnerable to the long-term complications of chronic esophageal eosinophilia. Alternatively, patients may not develop complications, but which patients will or will not develop these complications, how long it might take, and where the complications will develop anatomically are entirely unknown, since the natural history of EE has not been adequately characterized. Thus, the cost-benefit analysis of repeated endoscopies has not been determined.

In this regard, the obvious problem is that the only method currently available to determine the state of esophageal mucosal inflammation is endoscopy with mucosal biopsy (Gonsalves et al., 2006). While this procedure is relatively safe overall, several downsides do exist including the potential complications of conscious sedation or general anesthesia (hypoxia, allergic reactions to the medications, airway compromise) and risks of the procedure itself (esophageal perforation, bleeding and infection). Endoscopy with biopsy is limited in that each biopsy only provides an assessment of <0.001% of the total esophageal surface area. Endoscopy is costly and often is not covered by insurance companies when repeated as described above. It is also important to recognize that while EE is currently a recognized disease amongst most clinicians, an ICD-9 code for EE does not yet exist. This lack of "certification" of EE has created administrative confusion in terms of how to pay for endoscopy. Finally, endoscopy results in lost time from school or work.

Other proposed methods to analyze the esophageal mucosa include monitoring symptoms, radiological studies, and serum or stool analyses (Gupta et al., 2005). It is a well-recognized fact that symptoms do not necessarily correlate with evidence of histological activity (Liacouras et al., 2005). To date, no serological or stool analysis has provided reliable and durable findings that correlate with and are consistently predictive of histological evidence of disease remission or progression. Aside from a recent study showing correlations for measurements of absolute eosinophil counts, plasma EDN and eotaxin-3 levels with disease status (Konikoff et al., 2006), preliminary studies measuring eosinophil granule cationic proteins in the serum of affected patients have failed to find significant correlations with disease activity. Taken together, these findings indicate that a minimally invasive, inexpensive, safe, reliable and accurate method for direct measurement of esophageal inflammation is needed for initial diagnosis and post-treatment management of patients with EE.

e. Novel Minimally Invasive Method for Assessment of Esophageal Inflammation in Patients with EE The Enterotest™ was first used as a minimally invasive method to identify infectious organisms (*Giardia lamblia*) in the duodenum of suspected patients (Gracey et al., 1977; Thomas et al., 1974). The Enterotest™ consisted of a weighted gelatin capsule that was filled with a 90 cm nylon string. The end of the string extruded out of one end of the capsule (see FIG. 1). The patient was asked to swallow the capsule while holding on to the end of the extruded string. As the capsule passed through the esophagus, stomach and duodenum, it left a trail of the string, the end of which was taped to the patient's cheek. After a period of time, the gelatin capsule dissolved, leaving the string free in the duodenum to which parasites within the intestinal mucosa would adhere. At a defined period of time, the string was then pulled back out of the mouth and the mucous and secretions on the distal end of the string were assayed for the presence of adherent parasites.

The proximal part of the Enterotest™ string could be used to assess esophageal inflammation associated with EE and have referred to this as the Esophageal String Test (EST) throughout this proposal. Benefits of the EST include: (1) ease of administration—no preparation/anesthesia required, (2) inexpensive—approximately <$20/capsule, (3) expansive—allows for evaluation of the entire length of the esophagus, not just a few sampling sites (4 biopsies=<0.01% of esophageal surface area), (4) safe—the only side effect may be discomfort or gagging when the capsule is first swallowed, (5) easily accessible—does not require an endoscopy suite. Preliminary results show that: (1) blood eosinophils and their granule cationic proteins interact with the EST in vitro and can be measured in a dose-response manner, (2) further in this regard, the EST detects increased secretion of granule cationic proteins as elaborated by IL-5-activated compared to resting blood eosinophils, and (3) in another esophageal inflammatory disease (GERD), both inflammatory proteins and mRNA (i.e., IL-8) can be measured in vivo using the EST, and correlates with the degree of esophageal inflammation.

Definitions

Unless defined otherwise, all technical and scientific terms used herein have the same meaning as commonly understood by those of ordinary skill in the art to which this invention pertains.

The term "assessing" includes any form of measurement, and includes determining if an element is present or not. The terms "determining," "measuring," "evaluating," "assessing" and "assaying" are used interchangeably and may include quantitative and/or qualitative determinations.

The phrase "diagnosing or monitoring a disease of the esophagus" as used herein refers to a method or process of determining if a subject has or does not have a disease of the esophagus, or determining the severity or degree of a disease of the esophagus.

The term "subject" as used herein refers to any member of the animal kingdom, preferably a human being.

The terms "treatment," "treating," "treat," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition.

Various biochemical and molecular biology methods referred to herein are well known in the art, and are described in, for example, Sambrook et al. (2001) and Ausubel et al. (1994).

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The string test was administered to a patient with reflux esophagitis and left in place for 1 and 12 hours. The first 10-20 cm of the string was pulled out from the capsule and the end of the string was secured between the fingers. The capsule and remaining string were swallowed with water and the string in the fingers was taped to the cheek. After the predetermined period, the taped string was removed from the cheek and the string retrieved from the intestinal tract. Following removal, the contents of the string were assessed for the presence of inflammatory proteins and RNA. The entire string was placed either in protein buffer, RNA stabilizing solution or formalin. After 1 and 12 hours in the esophagus, elevations of interleukin-8 and TNFα-protein were identified by Mesoscale and ELISA technology. In these studies, protein was extracted from the string, and the soluble product was placed in the well of a 96-well plate for analysis. Following placement of the soluble product in the well of the plate, a series of incubations and washes with target antibodies and buffers took place. Finally, the plate was placed in a specialized detection equipment for quantitation.

Example 2

Identification of Microbial Flora from EST. Identification and enumeration of esophageal and oral bacterial population by selective culture.

Figure 3A:
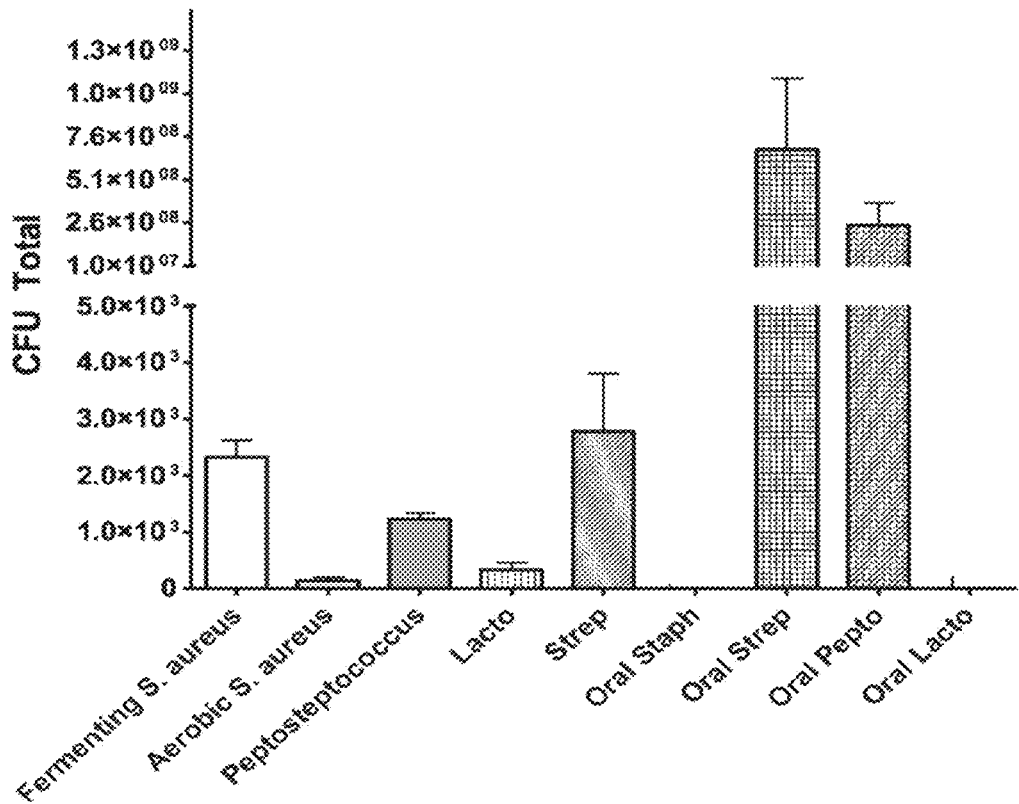
FIGS. 3A-3B. Microbiota in the esophagus and mouth of two subjects. Total colonies isolated from strings resident in esophagus or mouth for 15 minutes. Secondary unidentified anaerobe cultured on CDC Blood Agar with PEA not counted. No *Enterococcus* detected. Bars are SEM derived from duplicate plates from single string incubated for 5 minutes in HBSS.
Figure 3B:
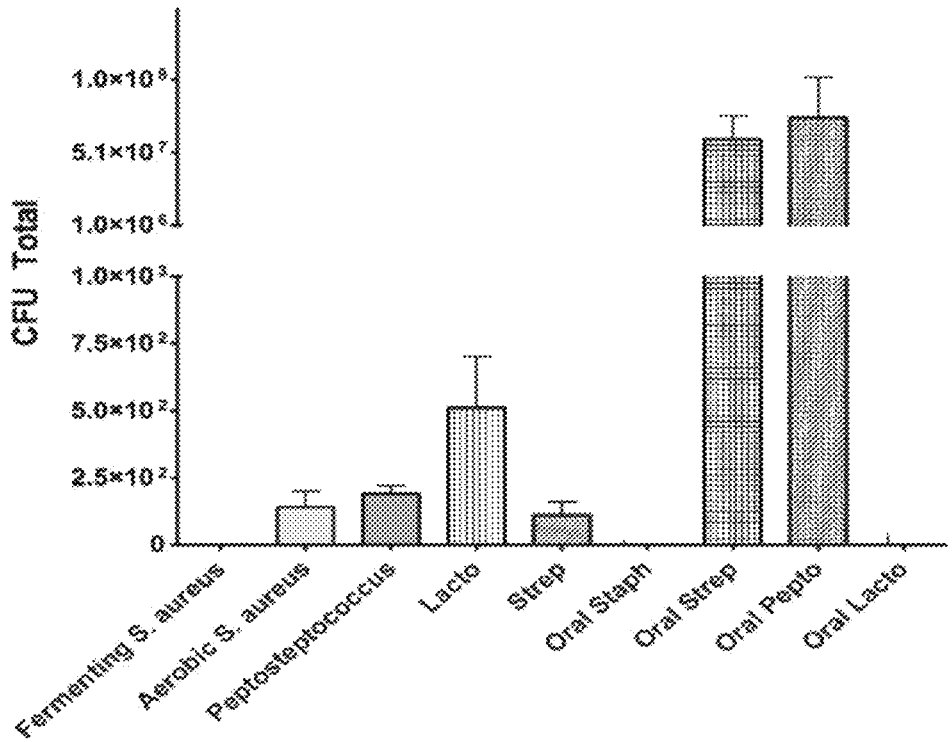

Microbial Culture. Strings were swallowed or remained in the mouth for 15 min A 5 cm piece of esophageal or oral string was aseptically transferred to 5 ml of sterile Hank's Buffered Salt Solution (HBSS) and vortexed for 30 sec before a 5 min incubation at RT. For nasal secretion collection swap was humidified in sterile saline; a nasal swab was collected using a BBL™ culture swab. String and nasal solution was vortexed again for 30 sec and the string removed. The solution was centrifuged for 15 min at 4750 rpm. Supernatant was aspirated and the pellet was resuspended in 1 ml of sterile HBSS. Dilutions up to $10^{-5}$ were performed and 50 ml of non-diluted samples or $10^{-5}$ dilution was plated in duplicate onto selective media. Plates were incubated at 37° C. overnight in aerobic or anaerobic (BD Bioscience Gas Packs) conditions. Plate colonies were then enumerated and total Colony Forming Units (CFU) were calculated. *Staphylococcus* sp, *Streptococcus* sp, *Lactobacillus* and *Peptostreptococcus* were cultured respectively on Mannitol salt agar, Selective *Streptococcus* agar, Difco lactobacilli MRS agar and CDC anaerobe blood agar with Phenyl Alcohol (Becton Dickinson). See FIG. 3.

Figure 4A:
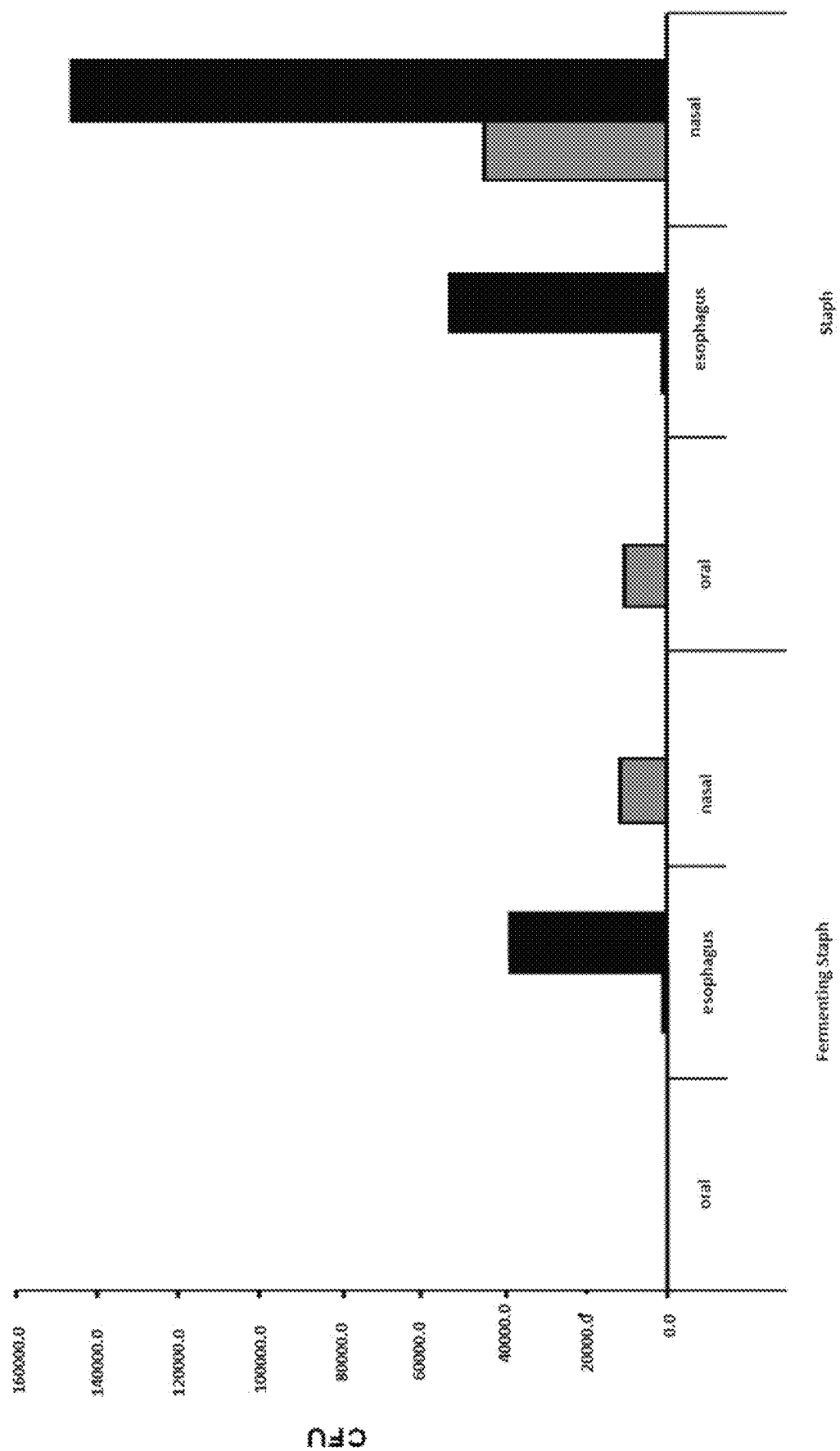
FIGS. 4A-B. Microbiota in the esophagus, nose, and mouth from 2 subjects.
Figure 4B:
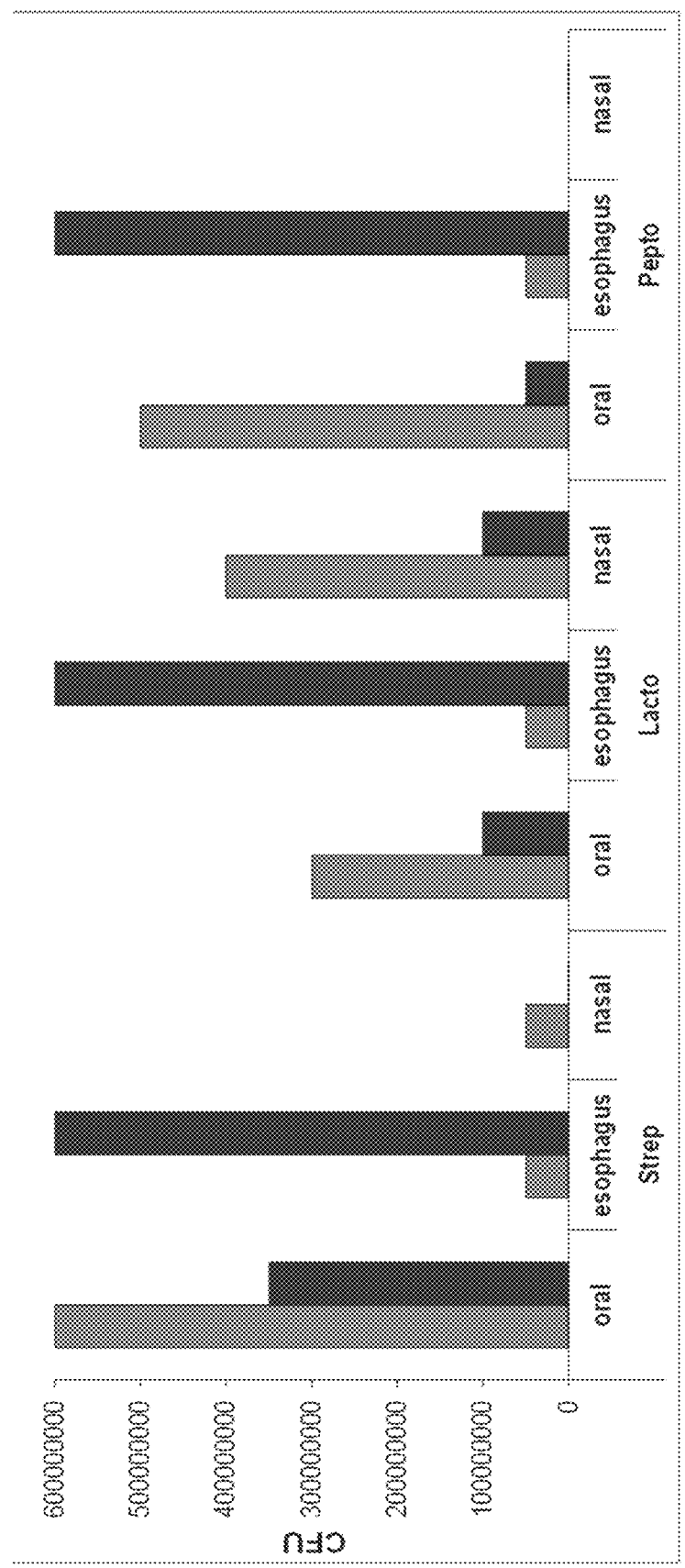
Figure 5:
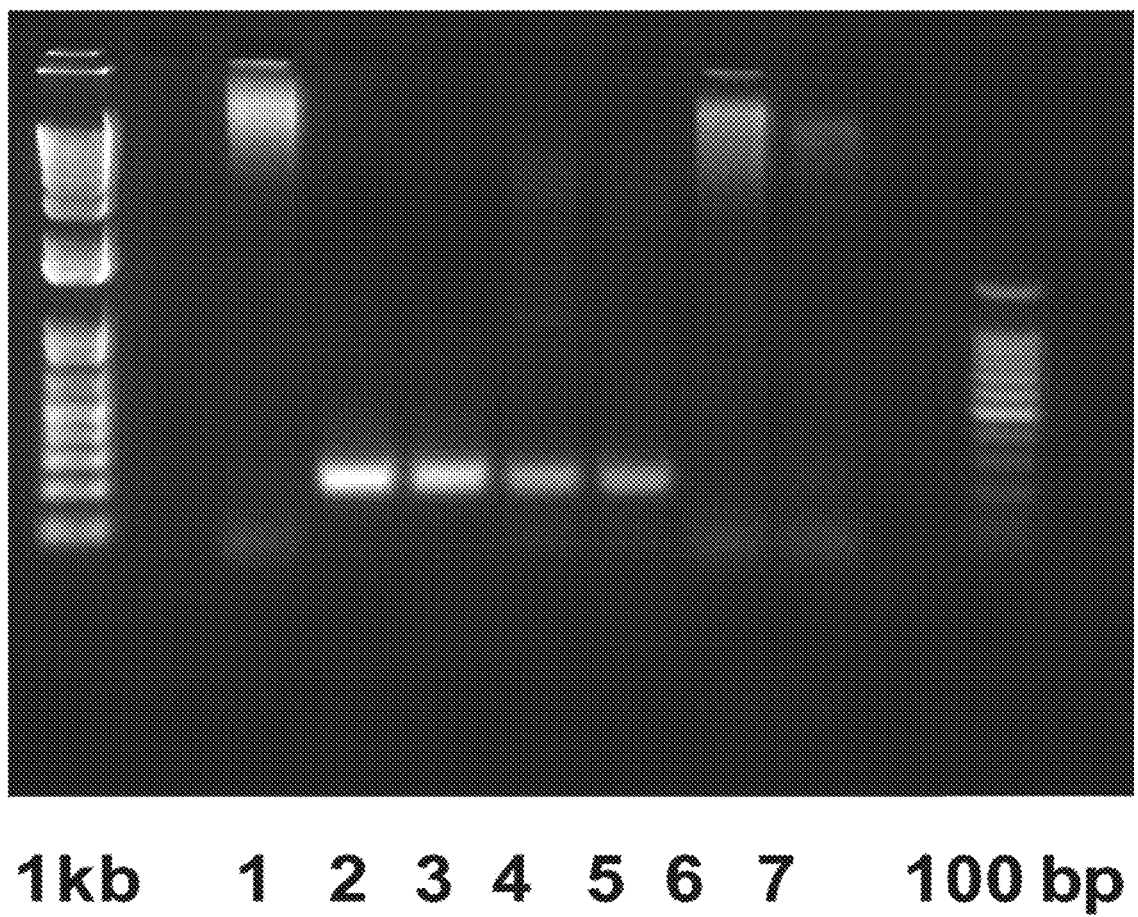
FIG. 5. PCR amplification of esophageal bacterial DNA. 16S rDNA gene. Lane 1-negative control sigma $H_2O$. Lane 2-40 µl bacterial DNA from string (S). Lane 3-40 µl bacterial DNA from string (Z). Lane 4-10 µl bacterial DNA from string (S). Lane 5-10 µl bacterial DNA from string (Z). Lane 6-1 µl bacterial DNA from string (S). Lane 7-1 µl bacterial DNA from string (Z). S DNA concentration of 1.32 ng/µl in 200 µl Z DNA concentration of 2.70 ng/µl in 200 µl 40 cycles performed at 95° C. for 3 min, 94° C. for 30 sec, 56° C. for 30 sec, 70° C. for 60 sec, and 72° C. for 6 min.

DNA Purification. Strings were incubated in 180 ml of ATL lysis buffer (QIAGEN) containing 2 mg/ml lysozyme (Sigma), bacteria were lysed for 1 hour at 37.degree. C. Proteinase K was added in 200 ml of ATL lysis buffer (QIAGEN) and incubated for 1 hour at 56° C. Purification of total DNA was performed following the manufacturer's instructions (DNeasy Blood and Tissue KIT QIAGEN). See FIGS. 4A-B.

Example 3

Measurements of Eosinophil Derived Granule Proteins from the Esophageal String Test (EST) can Detect Histological Evidence of Esophageal Inflammation Associated with EE. Preliminary results show that supernatants derived from activated eosinophils adhere to the EST and that eosinophil derived granule proteins within these samples can be measured by Western blot and ELISA analyses. These findings support the technical feasibility for the EST to be used to measure eosinophil derived granule proteins contained in the esophageal lumen of patients with EE.

Detection of Eosinophil Granule Major Basic Protein-1 (MBP1) on EST Strings Incubated with Acidic Lysates of Resting Eosinophils.

Figure 7:
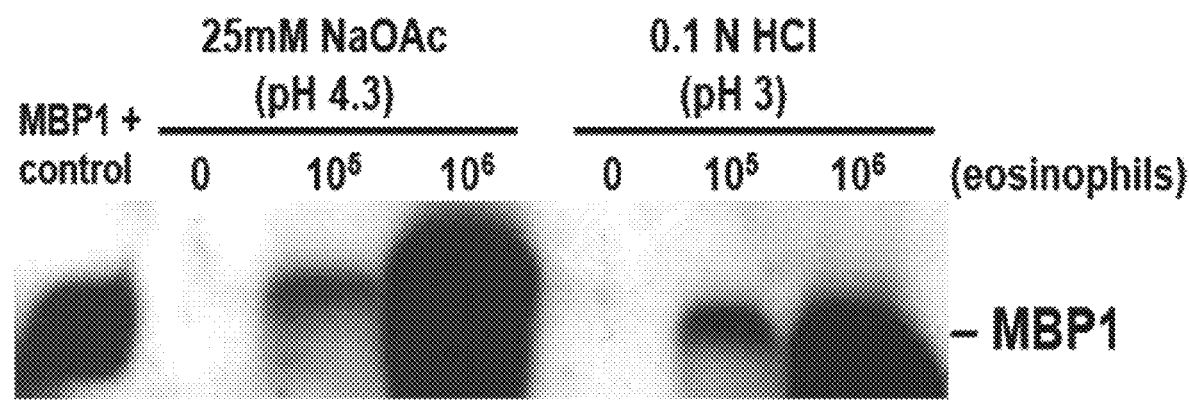
FIG. 7. Detection of eosinophil granule major basic protein-1 (MBP1) adsorbed to EST strings incubated with acidic lysates of blood eosinophils. Acidic sonicates of purified blood eosinophils were prepared by sonicating $1\times10^6$ or $1\times10^6$ cells in either 25 mM sodium acetate/acetic acid (NaOAc) buffer (pH 4.3) or 0.1N HCl (pH 3). The EST strings (2 cm lengths) were incubated with 0.5 ml eosinophil sonicates for 1 hr, the strings removed, blotted to remove excess fluid, boiled in SDS-PAGE sample buffer, and analyzed by SDS-PAGE and Western blotting for the presence of MBP1 adsorbed to the EST string. Purified MBP1 was used as the positive control for Western blotting.

In order to demonstrate the ability of EST string to detect eosinophil granule cationic proteins, purified blood eosinophils from normal subjects (>99% eosinophils) were used to prepare soluble acidic lysates by sonication of different numbers of eosinophils ($1 \times 10^5$ or $1 \times 10^6$ cells) in either 0.1N HCl (pH 3) routinely used to solubilize eosinophil granule cationic proteins from secondary granules, and a 25 mM sodium acetate/acetic acid (NaOAc) buffer (pH 4.3) routinely used for size exclusion chromatographic purification of these proteins. EST nylon fiber strings (2 cm lengths) were incubated with 0.5 ml of the eosinophil sonicates for 1 hr, the strings removed and blotted briefly until visibly dry, boiled in SDS-PAGE sample buffer, and analyzed by SDS-PAGE/Western blotting for the presence of MBP1 adsorbed to the strings (FIG. 7). Of note, the strings were purposefully not washed prior to boiling in SDS-PAGE sample buffer so as to simulate in vivo diagnostic performance of the Enterotest™ EST, in which strings are pulled from the GI tract and directly analyzed without further washing for the presence of adherent mucus and *Giardia lamblia* parasites. After 1 hr incubation, MBP 1 could be detected on EST strings by Western blotting using sonicates prepared from $1\times10^5$ eosinophils, with increased MBP 1 detected for sonicates of $1\times10^6$ eosinophils, both HCl and acetate buffer providing comparable MBP1 levels. These results demonstrate the ability of EST string to detect eosinophil MBP1 from soluble lysates of as few as $2\times10^5$ eosinophils/ml.

Figure 8:
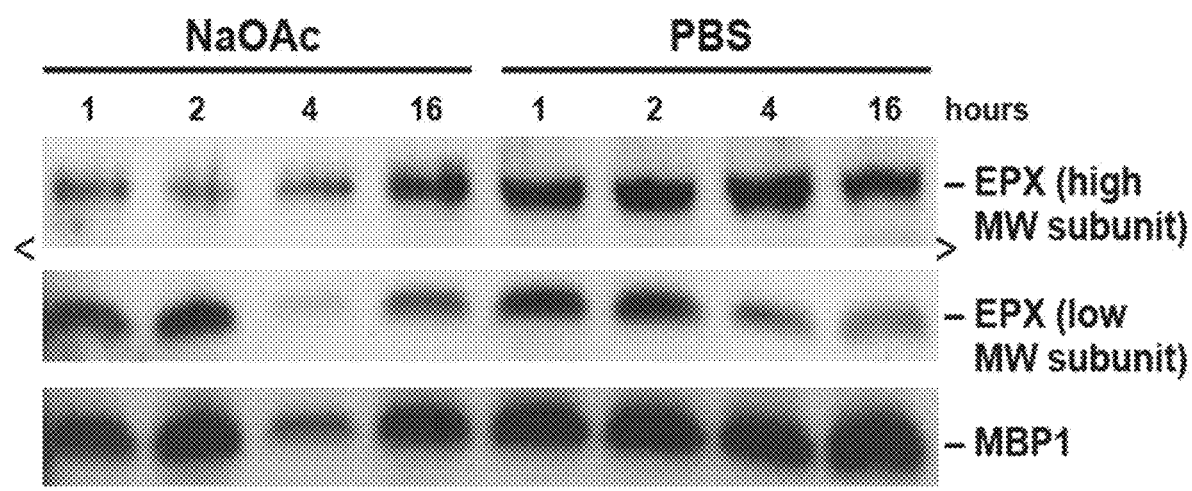
FIG. 8. Time course for detection of eosinophil peroxidase (EPO) and granule major basic protein-1 (MBP1) adsorption to EST strings. Incubated with sonicates of blood eosinophils. Lysates of purified blood eosinophils were prepared by sonication of $1\times10^6$ eosinophils in either 25 mM sodium acetate/acetic acid (NaOAc) buffer (pH 4.3) or in phosphate-buffered saline (PBS; pH 7.3). EST strings (2 cm lengths) were incubated with 0.5 ml of eosinophil sonicate for the indicated time points (1-16 hrs), the strings harvested, blotted to removed excess fluid, boiled in SDS-PAGE sample buffer, and analyzed by SDS-PAGE and Western blotting for the presence of EPO and MBP 1 adsorbed to the strings. The upper two panels from the same gel show both the high (about 52 kD) and low (141<d) molecular weight EPO subunits, and the lower panel, MBP 1. EPO and MBP 1 were detected on the EST strings within 1 hr, with somewhat more protein detected using PBS than NaOAc buffer sonicate. Incubation times longer than 1 hr did not increase the amount of adsorbed protein detected by Western blotting.

Time Course for EST String Detection of Soluble Eosinophil Granule Cationic Proteins. In order to determine the minimum amount of time required for detection of soluble eosinophil granule cationic proteins using the EST, 2 cm lengths of EST string were incubated with 0.5 ml of lysates of purified blood eosinophils that were prepared by sonication of $1\times10^6$ eosinophils in either 25 mM sodium acetate/acetic acid (NaOAc) buffer (pH 4.3) or in phosphate-buffered saline (PBS; pH 7.3) EST strings (2 cm lengths) for 1-16 hours. The strings were harvested by blotting to dryness as above, boiled in SDS-PAGE sample buffer, and analyzed by SDS-PAGE and Western blotting for the presence of EPO and MBP 1 adsorbed to the strings (FIG. 8). The upper two panels from the same Western blot show both the high (52 kD) and low (14 kd) molecular weight subunits of EPO, and the lower panel shows results for MBP1. Both EPO and MBP1 were detectable on the EST strings within 1 hr, with somewhat increased amounts of the proteins detected using lysates prepared in PBS compared to the acidic sodium acetate buffer. Incubation times longer than 1 hr did not significantly increase the amount of EPO or MBP1 adsorbed to the strings, suggesting that relatively short-term exposure of the EST strings in vivo may be sufficient for detection of the eosinophil granule cationic proteins.

Figure 9A:
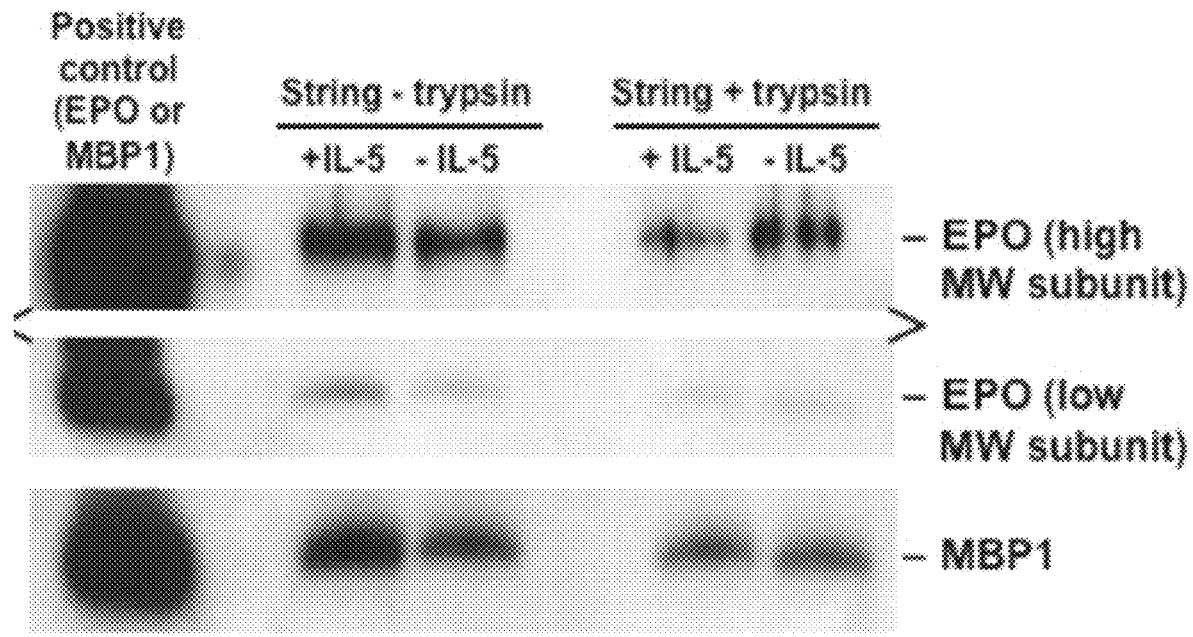
FIGS. 9A-9B. IL-5 activation of blood eosinophils results in increased eosinophil adherence and detection of eosinophil granule cationic proteins adsorbed to EST strings. Purified blood eosinophils ($1\times10^6$ cells) were incubated with 2 cm lengths of EST string for 1 hr in complete culture media containing 8% FBS with or without the addition of IL-5 (25 ng/ml) to activate eosinophil secretion. Strings were removed from the culture media, blotted to remove excess media, and some strings were briefly incubated in trypsin/EDTA to remove adherent intact eosinophils. Strings were then boiled in SDS-PAGE sample buffer and analyzed by SDS-PAGE/Western blotting for eosinophil peroxidase (EPO) and granule major basic protein-1 (MBP1) (left). Both MBP1 and the high (52kD) and low (14 k(D) molecular weight subunits of EPO are shown (left). Activation of eosinophils with IL-5 increased the amount of MBP1 and EPO detected on the EST strings (right), some of which was due to adherent intact eosinophils/HPF that were removed by the trypsin/EDTA treatment.
Figure 9B:
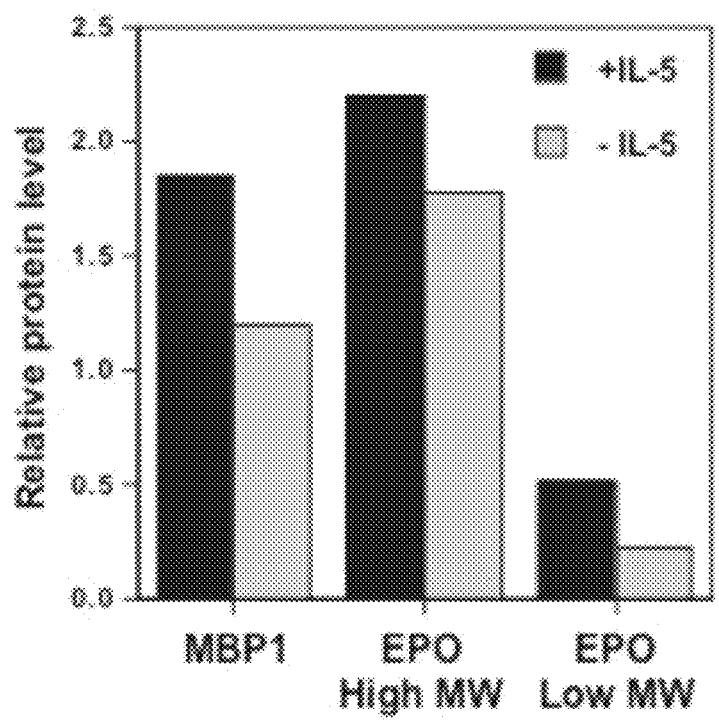

IL-5 Activation of Blood Eosinophils Increases Eosinophil Secretion and Detection of Eosinophil Granule Cationic Proteins Adsorbed to EST Strings. In order to determine whether the EST can differentially detect and measure granule cationic protein secretion from resting vs. cytokine-activated eosinophils, intact purified blood eosinophils ($1\times10^6$ cells) were incubated with 2 cm lengths of EST string for 1 hr in 0.5 ml of complete tissue culture media containing 8% FBS with or without the addition of IL-5 (25 ng/ml) to activate eosinophil secretion of MBP1 and EPO. The strings were harvested from the TC media, blotted to remove excess media as in the above experiments. Again, the strings were not washed to simulate their use in vivo, but half the strings were briefly incubated in trypsin/EDTA solution to remove adherent eosinophils. Strings were then boiled in SDS-PAGE sample buffer and analyzed by SDS-PAGE/Western blotting for EPO and MBP1 (FIG. 9). Both MBP1 and the high (.about. 52 kD) and low (14 kD) molecular weight subunits of EPO were detectable by Western blotting (FIG. 9, left). Of note, activation of the eosinophils with IL-5 modestly increased the amount of both MBP 1 and EPO detected on the EST strings (left and as quantitated on the right). Some of the MBP1 and EPO signal was due to IL-5 activated eosinophils (visualized by inverted phase-contrast light microscopy) that were adherent to and intercollated between the nylon fibers of the strings—data not shown, as evidenced by the decreased MBP1 and EPO signals for strings treated with trypsin/EDTA to remove the adherent cells. Importantly, these findings demonstrate the utility of the EST for detection of eosinophils and their secretion of granule cationic proteins as induced by eosinophil-active cytokines such as IL-5.

Figure 10:
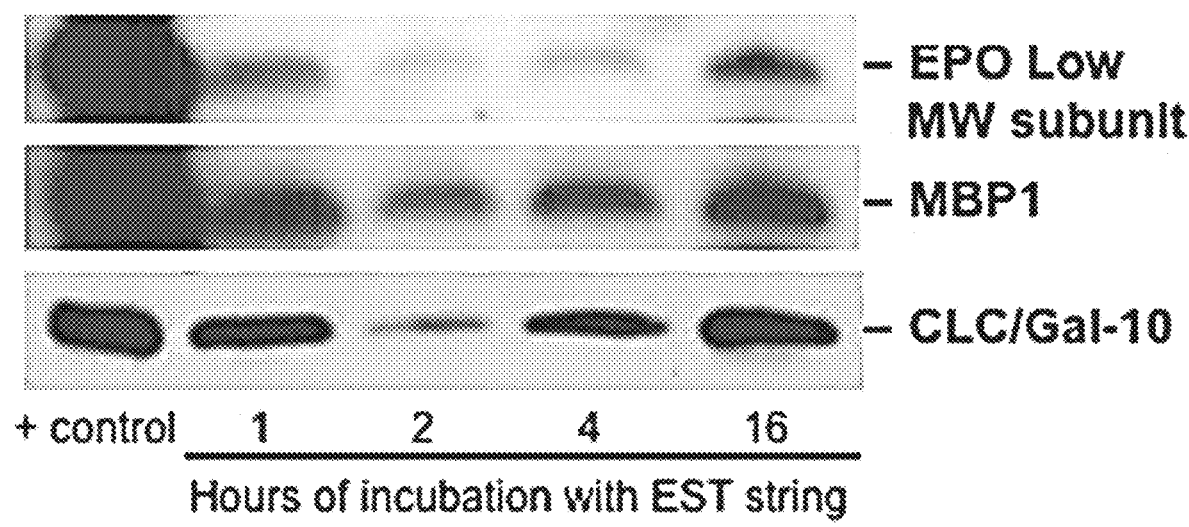
FIG. 10. Time course for detection of eosinophil granule proteins adsorbed to EST strings incubated with IL-5 activated blood eosinophils. Blood eosinophils ($1\times10^6$ eos @>99%) purified from normal subjects were activated with IL-5 (25 ng/ml) in the presence of EST strings (2.0 cm/time point) for the indicated time course in RPMI 1640 tissue culture media containing 8% FBS. Strings were transferred to SDS-PAGE sample buffer, boiled and analyzed by SDS-PAGE/Western blotting using antibodies to eosinophil peroxidase (EPO), major basic protein-1 (MBP1) and Charcot- Leyden crystal protein/Galectin-10 (CLC/Gal-10). Only the low molecular weight subunit of EPO is shown. Positive controls for Western blotting Included purified human EPO and MBP1, and for CLCgal-10, a lysate of AML14.3D10 eosinophils.

Time Course for EST Detection of IL-5-Induced Granule Protein Secretion by Blood Eosinophils. In order to determine the minimum amount of time required for EST detection of IL-5-induced eosinophil granule protein secretion, blood eosinophils ($1\times10^6$ cells @>99% purity) from normal subjects were activated with IL-5 (25 ng/ml) in the presence of EST strings (2.0 cm/time point) for 1-16 hours in 0.5 ml RPMI1640 tissue culture media containing 8% FBS. As above, strings were blotted to dryness and transferred to SDS-PAGE sample buffer, boiled and analyzed by SDS-PAGE/Western blotting using antibodies to EPO, MBP1 and CLC/Gal-10 (FIG. 10). These studies included Western blotting for CLC/Gal-10, since this highly expressed eosinophil cytosolic and primary granule protein constituent comprises an estimated 7-10% of total eosinophil protein (Ackerman et al., 2002; Ackerman et al., 1994; Ackerman et al., 1993), is the second most abundantly expressed mRNA in developing eosinophils (Plager et al., 1999), and most importantly, was recently shown to be amongst the 20 most highly up-regulated genes in cDNA micro array analyses of esophageal biopsy tissues obtained from patients with EE compared to GERD and normal control subjects (Blanchard et al., 2006b). Results showed that CLC/ga110, along with MBP 1 and EPO, were detected by EST within 1 hour of incubation of the strings with IL-5 activated eosinophils. For reasons that are unclear, the amounts of all three proteins detected decreased somewhat after 2-4 hours of eosinophil-string incubation, but by 16 hrs returned to levels comparable to those obtained after 1 hour. These results importantly demonstrate the ability of the EST approach to detect IL-5-induced secretion of three key eosinophil biomarkers in vitro, two of the major granule cationic proteins, and cytosolic CLC/Gal-10, recently shown to be markedly increased at the mRNA level in eosinophilic esophagitis (Blanchard et al., 2006b; Blanchard et al. 2006c).

Figure 11:
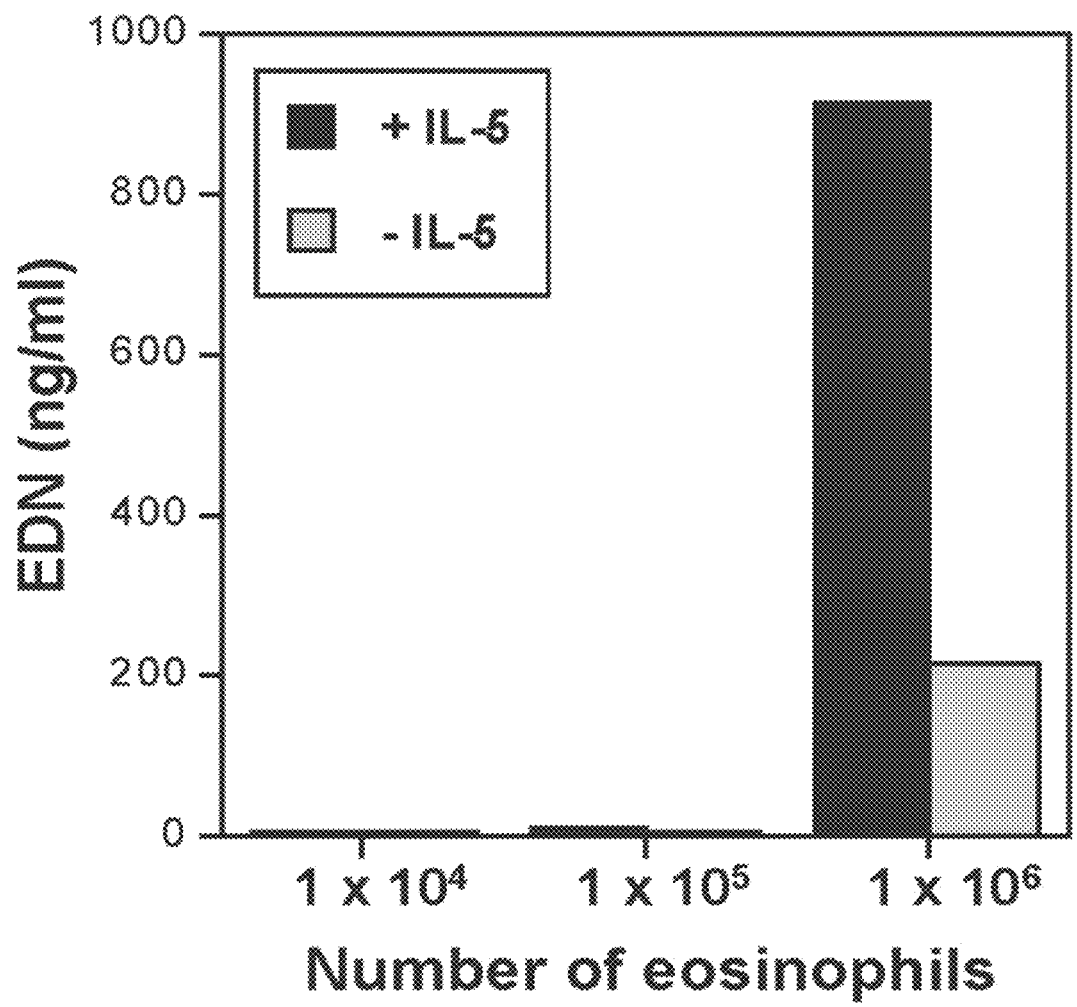
FIG. 11. EST detection of eosinophil derived neurotoxin (EDN) secretion by IL-5 activated eosinophils in vitro: measurement by EDN ELISA. Blood eosinophils ($1\times10^4$-$1\times10^6$ cells @>99%) purified from a normal subject were cultured with (+IL-5; 25 ng/ml) or without IL-5 (–IL-5) in the presence of EST string (2.0 cm) for 1 hour in RPMI 1640 tissue culture media containing 8% FBS. Strings were transferred to 0.5% NP-40 elution buffer (pH 6.0) for 30 min to elute secreted eosinophil granule proteins, and the amount of secreted EDN analyzed by ELISA (MBL Co., Ltd).

The EST can be used to detect IL-5-induced eosinophil granule protein secretion by ELISA assay. In order to determine whether the EST can be paired with more sensitive, quantitative and high throughput assays for eosinophil-associated biomarkers, e.g. ELISA assays, the above EST experiment was repeated and IL-5-induced eosinophil secretion of eosinophil-derived neurotoxin (EDN) was measured by ELISA. Blood eosinophils ($1\times10^4$-$1\times10^6$ cells @>99% purity) from a normal subject were cultured+IL-5 @ 25 ng/ml in the presence of EST string (2.0 cm/0.5 ml cultures) for 1 hour in RPMI 1640 tissue culture media supplemented with 8% FBS. To elute and solubilize adherent eosinophils and eosinophil granule proteins, the strings were removed, blotted to dryness, and transferred to 0.5% NP-40 elution buffer (pH 6.0) for 30 minutes, with vortexing at room temperature. The IL-5-inducible eosinophil expression of EDN eluted from the EST strings was analyzed by an EDN-specific ELISA (MBL Co., Ltd) (FIG. 11). As measured by ELISA, IL-5 induced >4-fold more detectable EDN than eosinophils incubated with EST strings in the absence IL-5. However, significantly less EDN was measured using 10-fold fewer eosinophils ($1\times10^5$ cells/0.5 ml/2 cm string), suggesting sensitivity lies between $1\times10^5$-$1\times10^6$ eosinophils under these conditions. Of note, a recent study by Konikoff and colleagues (Konikoff et al., 2006) showed that plasma EDN levels, along with absolute eosinophil counts and eotaxin-3 levels, were significantly correlated with esophageal biopsy eosinophil density, and may have value as non-invasive biomarkers for monitoring EE. Overall, these results demonstrate the feasibility of using more quantitative assays than Western blotting to quantitatively measure eosinophil biomarkers such as EDN on EST strings, supporting the use of ELISAs and more high throughput approaches, i.e. Mesoscale (see FIGS. 12-16), to quantitate Th1 (IL-2, TNF-α INF-γ and Th2 (IL-4, IL-5, and IL-13) cytokines and multiple eosinophil-associated biomarkers of interest including the eosinophil granule proteins (MBP, EPO, EDN, ECP), CLC/Gal-10, eosinophil-active cytokines (e.g., IL-5) and chemokines (eotaxin-3, some of which e.g., EDN, eotaxin-3) may have utility as correlates of esophageal eosinophilic inflammation (Konikoff et al., 2006).

Experimental Design and Methods

Determine if Measurements of Eosinophil Derived Granule Proteins from the Esophageal String EST can Detect Histological Evidence of Esophageal Inflammation Associated with EE. Presently, two large voids exist in the field of food allergic diseases in terms of eosinophilic esophagitis (EE) (Furuta et al., 2006). First, the pathogenesis of EE is not certain and knowledge is limited by the fact that repeated endoscopy with biopsies are necessary for any assessment of the inflammatory state in vivo. While at least one biomarker (epithelial-expressed eotaxin-3) (Blanchard et al., 2006a; Konikoff et al., 2006) has thus far been identified for EE, the EST offers an excellent opportunity to identify novel biomarkers that will expand the understanding of the pathogenesis of EE in a relatively simple, minimally invasive fashion. Second, clinical assessment of patients with EE is severely limited, again by the fact that, short of symptomatic assessment, endoscopy with biopsies is the only method currently available to determine diagnoses and the effectiveness of treatment. Again, the EST offers a minimally invasive tool for assessing esophageal inflammation. The EST or some modification thereof may offer diagnostic capabilities, e.g., in the identification of an EE proteome or transcriptome.

EST addresses these two relevant and timely problems in a novel and unique manner A goal is to associate the levels eosinophilic inflammation identified in endoscopically obtained mucosal biopsies with the levels of eosinophil-specific markers, the eosinophil derived granule proteins, measured using the EST in children with well-defined EE. EST-detected eosinophil derived granule proteins were used as the primary marker because of their specificity in the evaluation of patients with EE. EST results obtained from patients with EE are compared with those obtained from patients with normal esophageal histology to determine the sensitivity of the EST.

Preliminary studies showed that the EST can be used as a novel minimally invasive method to analyze esophageal inflammation. The EST binds eosinophils and eosinophil derived granule proteins in vitro in a time and concentration-dependent fashion that is enhanced by eosinophil activation with IL-5. In vivo studies demonstrate that the EST successfully measures protein and mRNA of associated pro-inflammatory cytokines in GERD.

Measure Eosinophil-Derived Granule Protein Levels Using ESTs in Patients with EE EST Administration. Any subject in whom an esophageal disease is suspected may be evaluated. Patients will swallow an EST (FIG. 2A) the night prior to an already scheduled clinically indicated endoscopy (12 hour time point). This time point has been established for at least three reasons. First, preliminary results demonstrate binding of eosinophil granule proteins within this time frame in vitro. Second, cytokines associated with inflammatory esophageal disease are able to adhere to the EST following an overnight incubation in situ in the esophagus. Third, since the patient will undergo anesthesia, the patient can ingest nothing for 4-6 hours before the procedure. While it is likely that the inflammatory markers will adhere to the EST at earlier time points as suggested by the preliminary in vitro and in vivo studies, 12 hours provides a reliable and safe amount of time for the EST incubation. Patients will be asked to swallow a capsule and the attached EST string will be taped to the cheek. At the time of the endoscopy, the doctor or research study nurse will remove the EST.

Processing the EST. Just prior to the endoscopy, ESTs will be removed and cut into pieces according to anatomical location, i.e., mouth, esophagus and stomach. Within the packaging for each EST is a pH indicator, that when applied to the EST, marks the EST with a color change that allows for identification of the part of the GI tract that the string had resided. For instance, the gastric section of the string changes to orange (acidic environment) and the esophageal section is blue green (alkaline environment) (FIG. 2B). The indicator is only applied to a small (<1 cm) part of the string and this portion will not be included in the analysis. The length of the string from the lips to the proximal oropharynx is to measured determine the oral section. Sections of the string will be measured to standardize the final data (i.e., pg of protein per ml per cm of string). Sections are then placed in an Eppendorf tube with either sample elution buffer for protein analysis or TRIZOL reagent for RNA isolation (Furuta et al., 2005). Samples will be immediately frozen and processed in batches of 10-20 to eliminate day-to-day variability in isolation techniques, and then stored at −80° C. for final protein or mRNA analysis.

Analysis of the EST. In this experiment, samples derived from the EST are only analyzed for the presence of eosinophil derived granule proteins. The reason for this is that it allows a primary set of markers that are specific for eosinophils. To date, eosinophilic enumeration is the benchmark for the histological aspect of diagnosis and treatment (Furuta et al., 2007). Measurements and comparisons of other inflammatory markers (cytokines, leukotrienes, etc.) may offer pathogenetic insights, but their relevance as a specific marker for tissue eosinophils is limited at this point. Thus, only eosinophil derived granule proteins are measured from EST samples and compare them to eosinophilic inflammation identified in the histological specimens.

Protein Analyses. The eosinophil derived granule proteins to be assayed in serum (or plasma as appropriate) and in the EST samples include MBP1, EDN, ECP, EPO, and cytosolic CLC/Galectin-10. The eosinophil protein analyses will be performed by double antibody RIAs (for MBP1, CLC-Gal-10) as previously performed (Ackerman et al., 1981; Ackerman et al., 1990; Ackerman et al. 1980), commercially available ELISAs (for EDN, ECP), a commercially available luminescence enzyme activity assay (for EPO), and Western blotting (all proteins as needed for confirmation). For all assays, results will be recorded quantitatively as protein level/ml of serum or plasma, or protein level/ml/cm string for the EST (for ELISAs or RIAs), and blots will be scanned and quantitated by comparisons to purified granule protein standard curves (as needed for Western blotting confirmation). In addition to this panel of eosinophil-specific protein markers, the levels of eotaxin-3 will be determined using a commercially available ELISA as previously reported for EE patients (Konikoff et al., 2006). Finally, the levels of eosinophil-expressed pro-fibrotic cytokines and growth factors that may contribute to the tissue remodeling (epithelial hyperplasia and fibrosis) seen in EE, including IL-1β, IL-6 and TGF-β will be measured using commercially available ELISAs as previously reported (Gomes et al., 2005) or by the Mesoscale multiplex assay system. All assays of the eosinophil granule cationic and other proteins include quality control (QC) samples with known low and high level concentrations of these eosinophil proteins to control for inter-assay variation, and these QC samples will be included in all assays of patient plasma and EST samples to standardize the detection limits and variability of each of the assays.

Statistical Analyses. Prevalence of eosinophil derived granule proteins will be summarized using the proportion of patients whose EST samples with detectable eosinophil derived granule proteins grouped by the patients with pathologically proven EE and those with normal histology. Ninety-five percent confidence interval will be used to quantify the precision of these estimates. Assuming that 15% of patients with normal histology and 60% of EE patients can be successfully enrolled, the sample size will be 150 EE patients and 66 patients with normal histology. There is no previous data for estimating the prevalence and hence the most variable case (i.e., the prevalence is 50%) is assumed for precision estimates. For these sample sizes, the error margin would be 12% and 8% respectively for patients with normal histology and patients with EE.

Determine the Associations of Eosinophil Derived Granule Protein Levels from EST with Histological Inflammation in EE Patients Assessment of Clinical and Mucosal Inflammation. Clinical symptoms will be recorded at the time of initial assessment and recorded according to standardized data sheets that include unidentifiable patient ID number, primary symptom, histopathological data (numbers of eosinophils in each biopsy, presence or absence of microabscesses and superficial layering), treatment, and whether primary symptom was affected by treatment (Walsh et al., 1999; Desai et al., 2005; Teitelbaum et al., 2002). Results will be recorded as the presence of primary symptoms and resolution of symptoms. Mucosal biopsies will undergo standard blinded analysis by staff pathologists. Results will be recorded as the number of eosinophils/HPF and the presence or absence of eosinophil microabscesses or superficial layering. Inter-observer variability will be assessed after approximately every 50 slides, discrepancies noted and resolved (Walsh et al., 1999; Desai et al. 2005; Teitelbaum et al., 2002; Nurko et al., 2004).

Statistical Analyses. Chi-square test will be used to assess the association of presence of eosinophil derived granule proteins from the EST with the presence of eosinophils/degranulation in biopsy tissue or with symptoms (yes/no) among EE patients. The discriminating ability of eosinophil derived granule proteins for the presence of EE or clinical symptoms of EE will be summarized with sensitivity and specificity. The association of presence of eosinophils with level of eosinophil derived granule proteins (a continuous variable) will also be assessed using logistic regression. Receiving operational characteristics (RPC) curve will be used to examine the discriminating ability of eosinophil derived granule proteins for presence of eosinophils and determine the optimum cutoff for clinical use. For the expected sample size, there will be 80% power to detect statistical significance at the 5% level even if the EE patients have 20% higher prevalence of eosinophil derived granule proteins than patients with normal histology. Also, there will be 80% power to detect statistical significance if the sensitivity is 15% larger than the usual minimum acceptable cut off of 75% or if the specificity is 14% higher than the usual minimum acceptable cutoff of 80%.

Example 4

Preliminary results demonstrate that the EST can specifically detect high levels of IL-8 mRNA and protein associated with reflux esophagitis. The EST can be used as a minimally invasive in vivo test to identify inflammatory molecules potentially responsible for the pathogenesis of EE, and to monitor the ability of treatment to modulate this inflammation.

In Vivo Assessments of the EST for Detection of Biomarkers of Esophageal Inflammation. In order to demonstrate feasibility for using the EST to measure protein and mRNA biomarkers of esophageal inflammation in vivo, a number of Enterotest™/EST assessments were performed in a well-defined patient with a confirmed diagnosis of gastrointestinal inflammation due to gastroesophageal reflux disease (GERD), demonstrating increased levels of IL-8 at both the protein and mRNA levels compared to other inflammatory cytokines in the proximal and distal esophagus, but not in other locations in the GI tract, and decreased expression of IL-8 following treatment with a proton-pump inhibitor. IL-8 has been previously shown to be increased in tissues and BAL fluid associated with GERD with levels diminishing following treatment (Isomoto et al., 2004; Oh et al., 2007; Thibeault et al., 2007; Yoshida et al., 2004). These studies demonstrate the ability of the proposed EST to quantitatively measure relevant biomarkers of esophageal inflammation and their decrease during disease remission following treatment, providing proof-of-principle in vivo for its use in the proposed exploratory studies of eosinophilic inflammation and biomarkers of IgE-mediated responses in patients with EE.

Figure 12A:
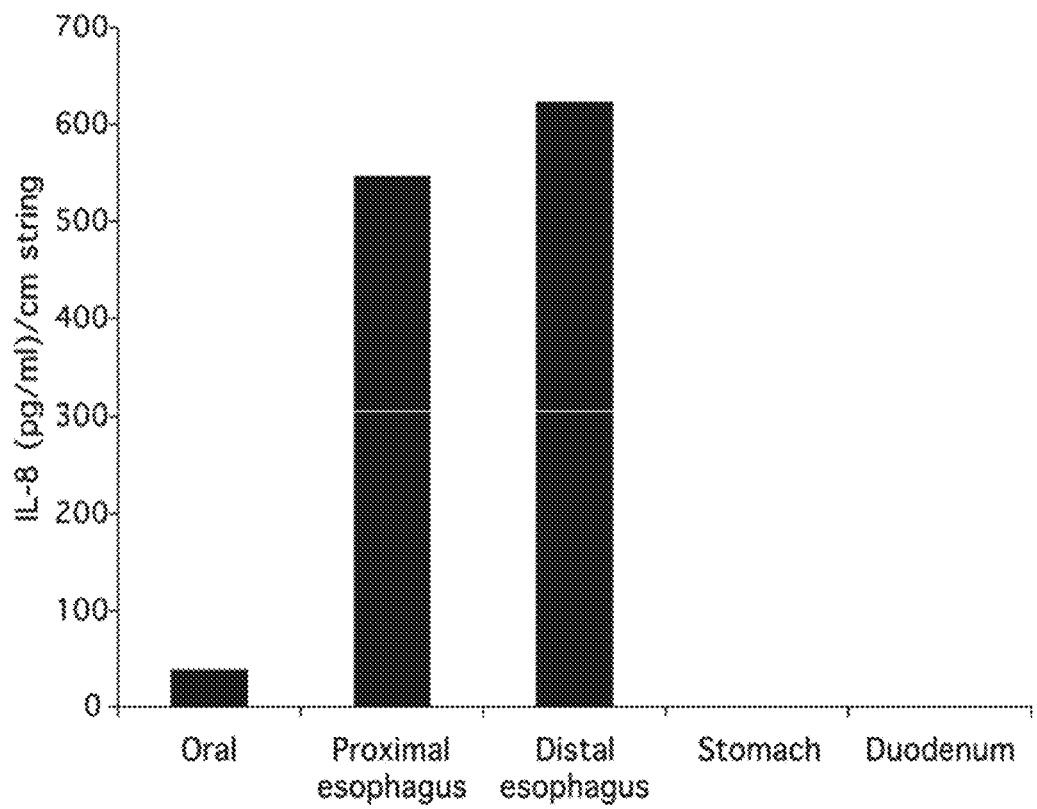
FIGS. 12A-B. IL-8 protein levels determined by the Enterotest™ in a patient with well-defined GERD.
Figure 12B:
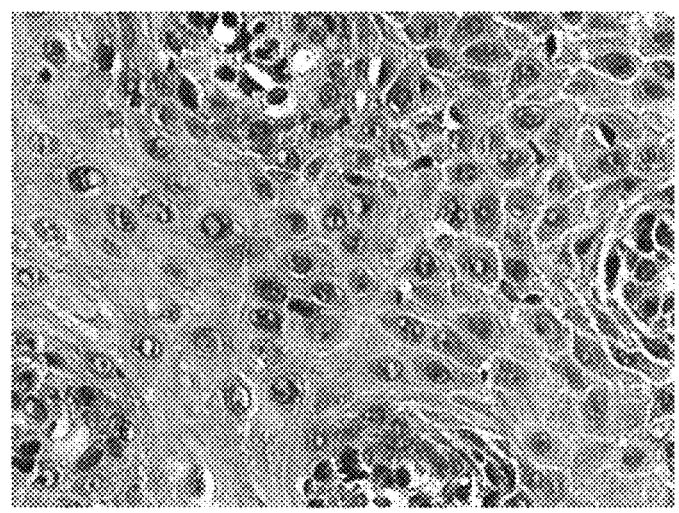

Detection of High Levels of IL-8 Protein in the Esophagus by the Enterotest™ in a Patient with GERD. An adult with well-characterized Gastroesophageal Reflux Disease (GERD) was studied. Endoscopic analysis was grossly normal but mucosal biopsy showed histological evidence of mild eosinophilic inflammation (FIG. 12A) and basal zone hyperplasia. In addition, 24 hour pH monitoring of the distal esophagus was abnormal with >18% pH<4 and >200 episodes of pH<4 measured, solidifying the diagnosis of GERD. The Enterotest™ was performed and the string removed after 12 hours and cut into oral, esophageal (proximal and distal), stomach and duodenal segments. These anatomical locations of the EST segments were identified by pH measurements on the string (FIG. 2B), i.e., distal section=alkaline pH in the duodenum, middle section=acid pH in the stomach, proximal section=alkaline pH in the esophagus. Protein secretions were eluted from the string segments for measurement of IL-8 protein using the Mesoscale™ assay (FIG. 12B). Mesoscale is a high throughput technology that allows multiplex analysis of individual samples for up to 10 different proteins simultaneously. The results clearly show the ability of the EST to detect expression of IL-8 protein in both the distal and proximal esophagus, but not in the mouth, stomach or duodenum of this patient during active inflammation due to reflux esophagitis. Results for the Mesoscale IL-8 measurements were verified using an IL-8 ELISA (data not shown).

Figure 13:
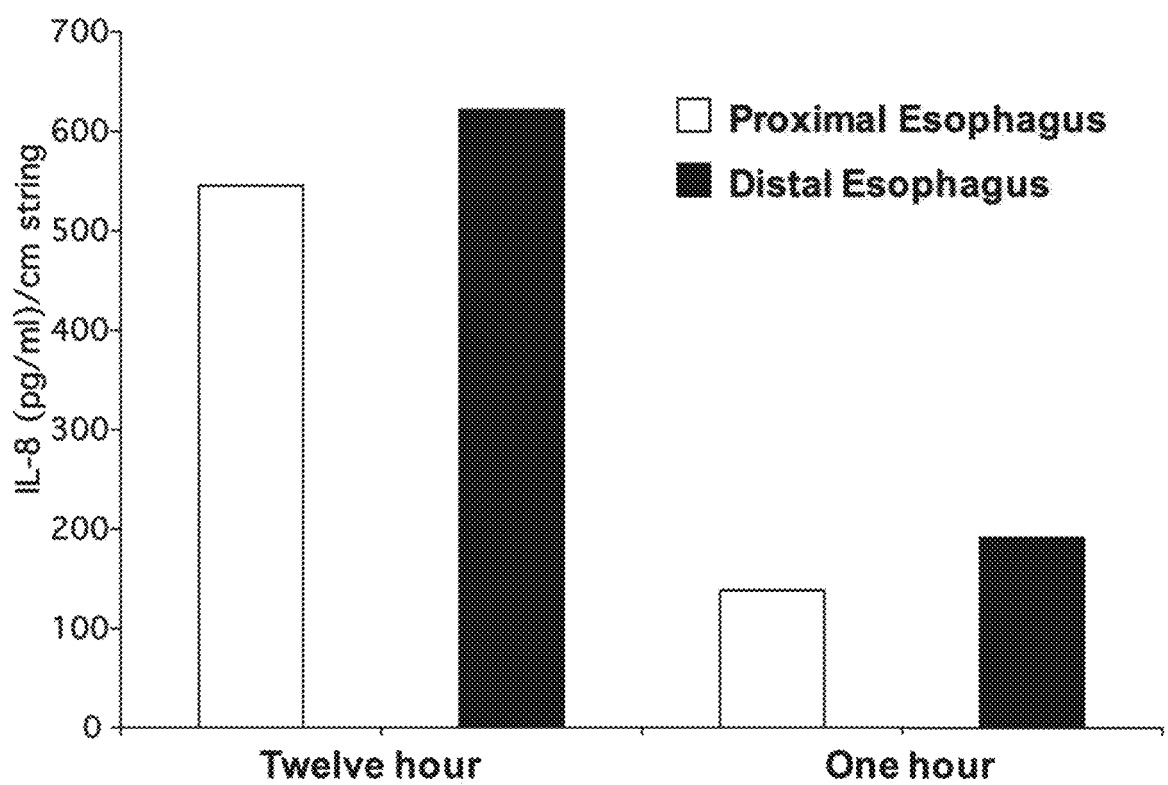
FIG. 13. Time course for IL-8 protein measurement by EST in a patient with GERD. Two separate ESTs were performed in a well-defined patient with GERD. The strings were removed after 12 hours and 1 hour periods. Upon removal, the esophageal segment of the EST was cut into proximal and distal halves and the adherent secretions eluted with sample buffer. Secretions were assayed by Mesoscale for IL-8 protein content, expressed as pg IL-8/ml/cm of eluted string.

Time Course for Detection of IL-8 Protein in the Esophagus Using the EST in a Patient with GERD. In order to establish a time course for the detection of esophageal inflammation by the EST, two ESTs were performed on different days in the same patient with well-defined GERD. The strings were removed after 1 or 12 hours, the esophageal segments identified using pH assessments as above, and cut into proximal and distal halves. The adherent secretions were eluted and assayed by Mesoscale for IL-8 protein content (FIG. 13). IL-8 was clearly detectable in both the proximal and distal esophagus after the string was in the esophagus for 1 hour, but IL-8 levels were .about. 3-fold higher when the string was left in place for 12 hours (FIG. 13). These results show that the EST is capable of detecting the presence of inflammatory cytokines in situ in as little as 1 hour, with increased levels detected after longer EST periods.

Figure 14:
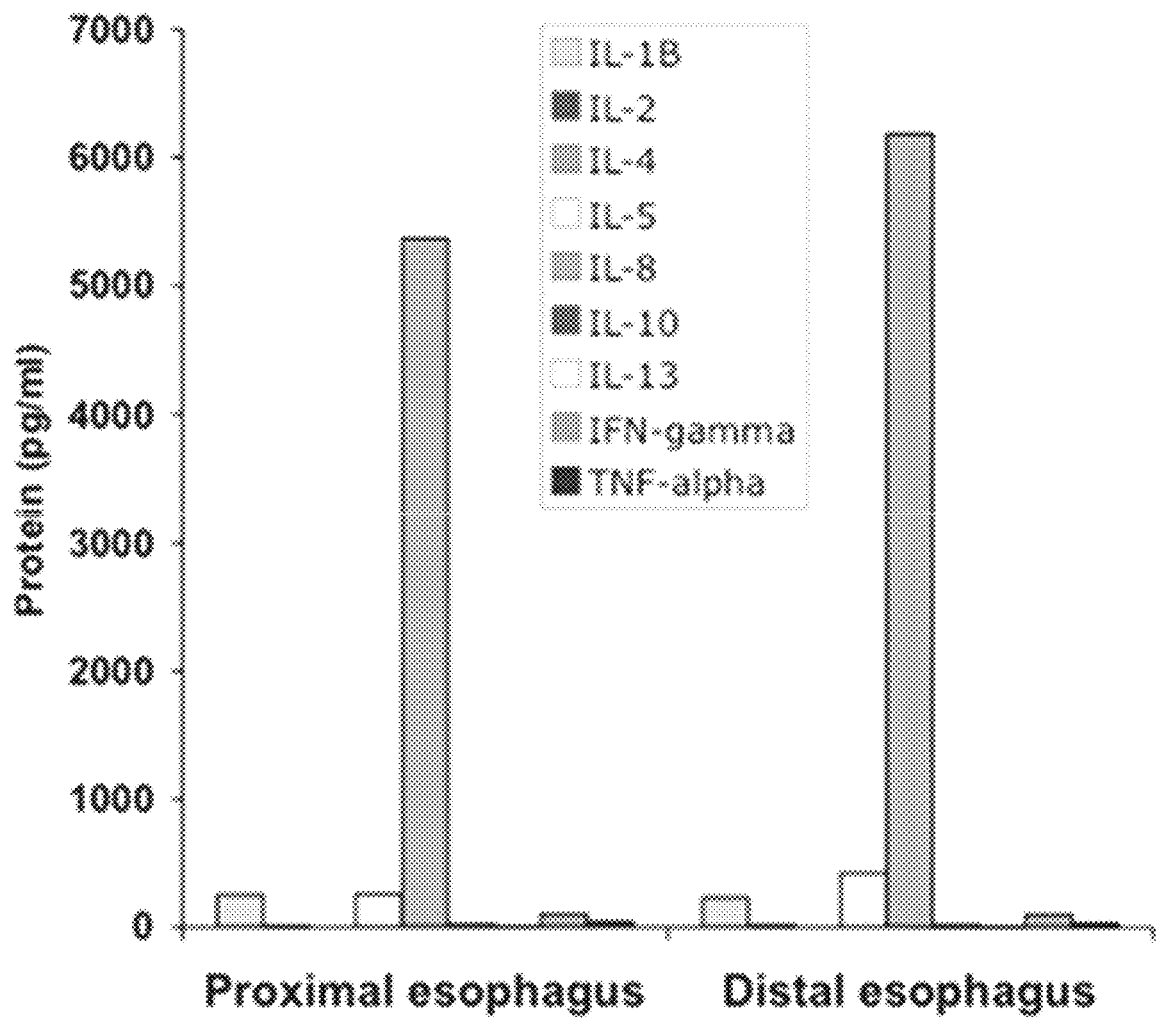
FIG. 14. Increased IL-8 compared to other inflammatory cytokines as determined by EST in a patient with GERD. EST was performed in a well-defined patient with GERD and the string removed after 12 hours. The esophageal string segment (based on pH probe and length measurements) was cut into proximal and distal halves, the adherent secretions eluted with sample buffer, and secretions assayed by Mesoscale for pro-inflammatory cytokines (protein). Note: IL-8 levels in this figure are higher since cytokine levels are reported as pg/ml instead of pg/ml/cm of string as in other figures.

Increased IL-8 Compared to Other Inflammatory Cytokines as Determined by EST in a GERD Patient. EST was performed in a well-defined patient with GERD and the string removed after 12 hours. The esophageal string segment (based on pH probe) was cut into proximal and distal halves, the adherent secretions eluted with sample buffer, and the secretions assayed by Mesoscale for pro-inflammatory cytokines as above. High levels of IL-8 were measured in the proximal and distal samples from the EST relative to other cytokines including IL-2, IL-4, IL-10, IL-13, and TNF-α. that were below detectable limits of the assay (FIG. 14). IL-1β, IL-5 and INF-γ were also detectable, but at much lower levels than IL-8 (FIG. 14).

Figure 15:
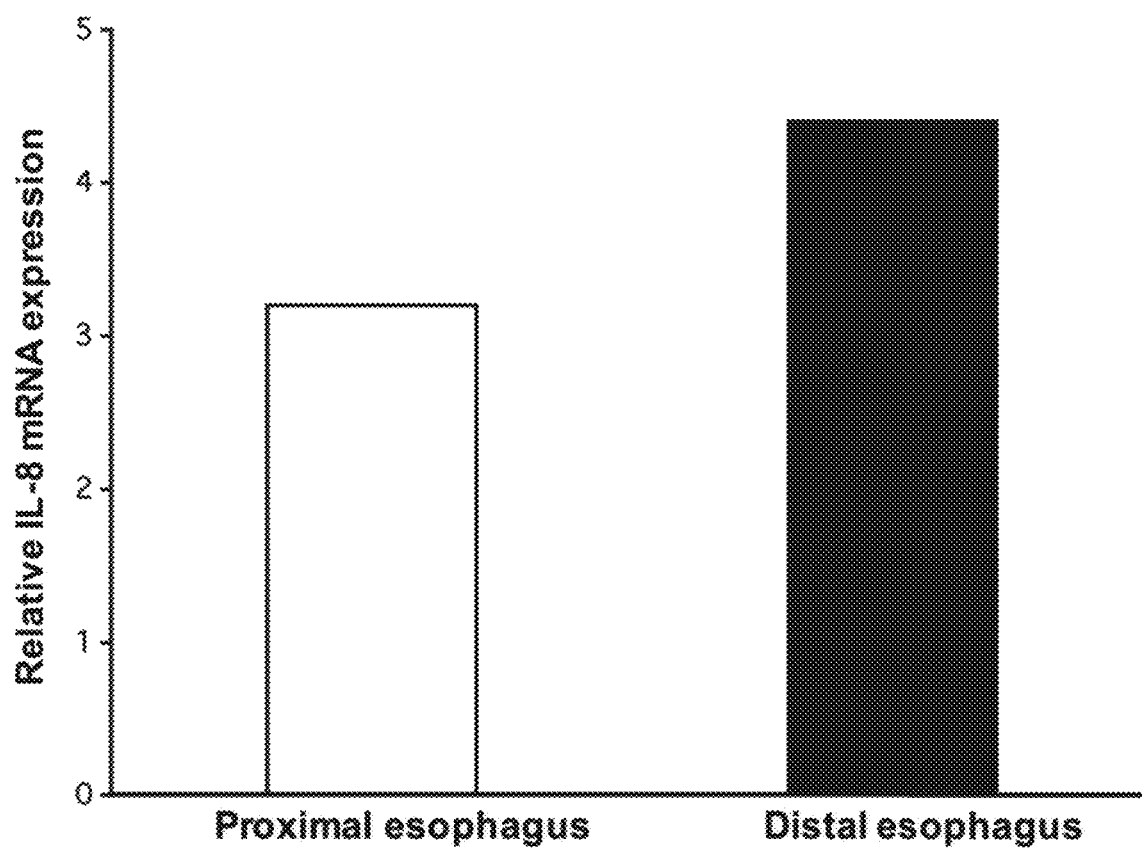
FIG. 15. IL-8 mRNA levels determined by Esophageal String Test (EST) in a patient with GERD. The EST was performed in a well-defined patient with GERD and the string removed after 1 hour. The string was cut into proximal and distal esophageal sections and total RNA isolated from the adherent cells. Quantitative RT-Q-PCR was performed using IL-8-specific primers and the results normalized to the expression of 13-actin in the samples.

Detection of IL-8 mRNA by EST in the Esophagus of a Patient with GERD. The same GERD patient as above performed a 1 hour EST and total RNA was extracted from the EST utilizing TRIZOL extraction techniques immediately after harvesting the string. Quantitative RT-Q-PCR was performed utilizing primers specific for IL-8 and normalized to the expression of β-actin determined using β-actin-specific primers (FIG. 15). Results show that the EST detected IL-8 mRNA in the both proximal and distal esophageal samples, consonant with previous reports of IL-8 expression in tissue sections in GERD, and importantly, support the technical ability of the EST to retain cells from the esophageal lumen for detection of inflammatory cell biomarker mRNAs.

Figure 16:
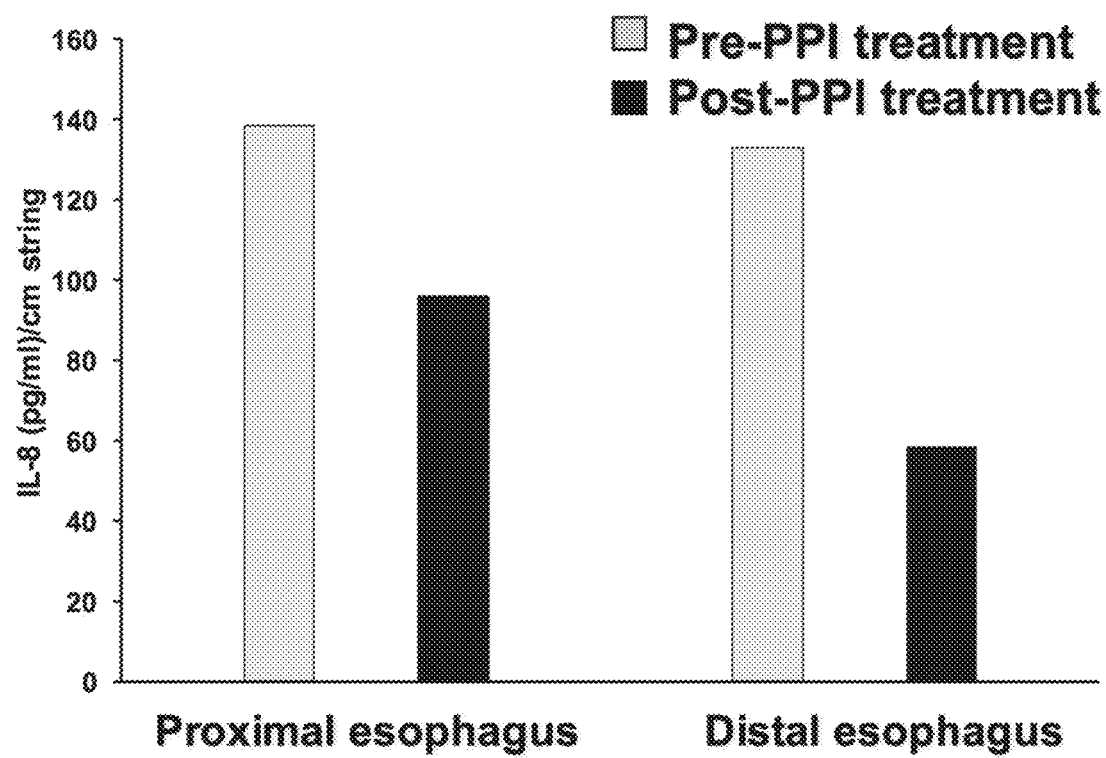
FIG. 16. IL-8 protein levels measured by EST in patient with GERD before and after treatment. The EST was performed in a well-defined patient with GERD before and after treatment with a proton pump inhibitor (PPI). The EST string was removed after 1 hour, the esophageal segment identified by pH and length and out into proximal and distal halves, and secretions eluted and assayed by Mesoscale for IL-8 protein. Results are expressed as pg/ml IL-8/cm eluted string.

Detection of Decreased IL-8 Levels by EST in a Patient with GERD Following PPI Treatment. The EST was performed in a well-defined patient with GERD before and after treatment for one month with a proton pump inhibitor (PPI). For both ESTs, the string was removed after 1 hour, the esophageal segment cut into proximal and distal halves, the luminal secretions eluted and assayed by Mesoscale for IL-8 protein, and results expressed as pg/ml IL-8/cm eluted string (FIG. 16). The EST-detected levels of IL-8 protein decreased by about 32% and 55% compared to the pre-treatment samples for measurements in the proximal and distal esophagus, respectively, demonstrating the feasibility for using the EST to monitor treatment-induced changes in biomarkers of esophageal inflammation, as proposed for studies of the effects of nutritional and corticosteroid treatments on esophageal inflammation in patients with EE.

Taken together, these preliminary results support a role for the EST in identifying and quantitating biomarkers of esophageal inflammation at both the protein and mRNA levels in an anatomically and cytokine specific fashion. In addition, they demonstrate how the EST can be used to follow treatment-induced changes in inflammatory responses within the esophageal lumen.

Experimental Design and Methods

Another unmet need in the assessment and evaluation of patients with EE is that except for endoscopy with biopsy, no other method exists as a means for assessing adequacy of responses to treatment. Symptoms, blood/stool tests and endoscopic appearance do not necessarily correlate with the histological assessments of esophageal inflammation, and a minimally invasive tool is urgently necessary to aid in determining EE's natural history and treatment effectiveness. As such, the esophageal inflammatory milieu may be investigated with the EST before and after treatment (nutritional elimination diets or corticosteroid).

Eosinophil derived granule proteins were identified as primary targets in Example 3. While a body of literature suggests that IgE plays a role in the pathogenesis of EE, no prospective studies have yet determined IgE-associated markers in luminal secretions of patients with EE. Thus, CD23, FcεRI, and mast cell tryptase are measured to characterize the mucosa (immunohistochemical staining) and luminal secretions (Western blot analysis). CD23 is a cell surface molecule that has recently been reported capable of mediating epithelial transcytosis of IgE/allergen complexes for presentation and induction of mast cell activation (Li et al., 2006). This has been previously measured in stool effluents from patients with food allergic diseases. FcεRI is the high affinity receptor for IgE that is typically associated with mast cells and basophils (Fiebiger et al., 2005; Sabroe et al., 2002). While it has not been previously measured in intestinal secretions, preliminary evidence shows that it is increased in esophageal tissues in association with EE (unpublished data).

In this light, it is expected that the presence of these targets may be measured by EST in esophageal secretions. Tryptase is a mast cell/basophil product that provides clinical evidence of degranulation. Since mast cells are increased in the esophageal tissues affected by EE, it is expected that levels of tryptase will concordantly be increased in esophageal secretions and can be detected by EST. Second, previous studies support the hypothesis that EE is a Th2-mediated disease (Mishra et al., 2001; Mishra et al., 2000; Mishra et al., 2007). Affected tissues have eosinophils, increased IL-5 expression, and murine models support an IL-5 dependent response. Treatment of limited number of EE patients with anti-IL-5 (Mepolizumab™) have shown therapeutic responses that included up to a 50% decrease in the numbers of esophageal eosinophils (Stein et al., 2006). In contrast, some patients express increased TNF-α and do not respond to food elimination diets. As such, the definition of the inflammatory milieu will be important to further characterize the disease state and determine potential therapeutic targets.

To date, very little research has comprehensively examined the esophageal milieu associated with EE (Blanchard et al., 2006a; Straumann et al., 2001; Konikoff et al., 2006; Gupta et al., 2006a; Gupta et al., 2006b). One study determined that measurements of absolute peripheral blood eosinophil counts, plasma EDN and eotaxin-3 levels were associated with esophageal inflammation. Thus, the EST will be used to measure the above-noted inflammatory mediators in samples from the plasma-(peripheral site), mucosal tissue-(gold standard), EST (local assessment) to determine whether associations exist. Furthermore, these panels of inflammatory mediators measured by the EST before and after treatment will be compared to determine their usefulness in monitoring disease. Also, it is expected that comparisons of EST levels (pre- and post-treatment) will begin to identify potential inflammatory molecules impacted by designated treatments that may serve as diagnostic clues and/or biomarkers.

Measure Plasma, Esophageal Mucosal (Biopsy) and Luminal (EST) Quantities of Eosinophilic Inflammation, Mediators of IgE Inflammation, and Th1/Th2 Cytokines Pre-and Post EE Treatment Evaluation of EST. Inflammatory mediators associated with EE will be quantified from samples derived from three sources, plasma, tissue, and esophageal lumen before and after treatment. Samples will be obtained from EE patients and normal controls as in Example 3. Each sample will undergo the following analyses (method of analysis);

Blood/plasma—eosinophil count, eosinophil derived granule proteins (ELISA), CD23 (ELISA), FcεRI (ELISA), tryptase (ELISA), eotaxin-3 (ELISA), and Th1 [IL-2, TNF-α, IFN-γ] and Th2 [IL-4, IL-5 and IL-13] cytokines (Mesoscale).

Mucosal biopsy—eosinophil count, eosinophil derived granule proteins (immunohistochemistry-IHC), CD23 (IHC), Fc.ε.RI (IHC), tryptase (IHC), eotaxin-3 (mRNA), and Th1 [IL-2, TNF-α, IFN-γ] and Th2 [IL-4, IL-5 and IL-13] cytokines-(mRNA).

EST—eosinophil derived granule proteins (ELISA), CD23 (ELISA), FcεRI (ELISA), tryptase (ELISA), eotaxin-3 (ELISA), and Th1 (IL-2, TNF-α, IFN-γ) and Th2 (IL-4, IL-5 and IL-13) cytokines (Mesoscale).

Samples will be collected before and after 8-12 weeks of either nutritional elimination (dietary elimination of specific foods as determined by skin prick testing or elemental diet) or corticosteroid treatments (systemic or topical [inhaled/swallowed] corticosteroids) (Ngo and Furuta, 2005). Both of these treatments have been shown to provide effective and durable remission of clinical and histological features of EE when used for 4-12 weeks. As a part of the standard of care, an endoscopy will be performed at the end of treatment. ESTs will be provided to the patient at the end of treatment to be swallowed the night before the endoscopy.

Protein Analyses

ELISA—Most targets have commercially available ELISAs (Furuta et al., 2000; Furuta et al., 2001; Karhausen et al., 2004). Sources of ELISA or antibodies are noted here—CD23 (BD Bioscience), FcεRI (ELISA), Eotaxin-1,2,3 (R&D Systems), Tryptase (R&D Systems).

Mesoscale—Mesoscale™ technology (Gowan et al., 2007) is a multiplex quantitative system for analyzing up to 12 target proteins in a single well of a 96-well plate. This technology needs only 2 µl of sample/well and the 96-well format allows for high throughput sampling and analysis. Data are provided in a quantitative format as pg protein per ml. For the studies, standardized Th1/Th2 templates will be used to assess the presence of Th1 (IL-2, TNF-α, IFN-γ) and Th2 (IL-4, IL-5 and IL-13) cytokines.

Immunohistochemistry—Tissue sections will undergo immunohistochemical analysis with specific antibodies as described above; antibodies for ELISA are also available for immunohistochemical analysis as previously described (Walsh et al., 1999; Desai et al., 2005; Teitelbaum et al., 2002). Briefly, all specimens will be formalin-fixed, paraffin-embedded, cut serially and either stained with hematoxylin and eosin or used for immunohistochemical studies. For immunohistochemical staining, sections will be dewaxed, rehydrated, peroxidase activity quenched, blocked and incubated with primary antibody and then secondary antibody. Color reaction will be then developed using the diaminobenzidine method and counterstained with hematoxylin, dehydrated, and mounted. Appropriate positive and negative controls will be included in each staining reaction. Quantification of positively stained cells for each of the selected antibodies will be performed.

RNA Analyses

Tissues will be homogenized with TRIZOL reagent to isolate total RNA that will then undergo reverse transcription and Q-PCR analysis using a BIORAD Real-Time iCycler PCR instrument. Primers for Th1 (IL-2, TNF-α, IFN-γ) and Th2 (IL-4, IL-5 and IL-13) cytokines have been purchased from Invitrogen.

Statistical Analyses

Linear regression will be used to model the percent change in quantity of histological eosinophilic inflammation with the change in marker level. Multiple linear regression will be used to assess the relationship of multiple markers with the pathological outcome simultaneously.

Determine Associations of Pro-Inflammatory Milieus as Measured by EST with Clinical State.

Pre- and post-treatment inflammatory markers levels as determined by EST will be compared with the patient's primary symptoms. Patients' symptoms will be recorded before and after treatment as improved, the same and worse.

Statistical Analyses. Chi-square test will be used to test the association of change in symptom (improved, same, worse) and change in biomarker (increased, same, decreased). Proportion odds model will be used to examine the association of multiple markers with the clinical status simultaneously. Separate analysis will be done for EE patients and those with normal histology.

All of the methods and apparatus disclosed and claimed herein can be made and executed without undue experimentation in light of the present disclosure. While the compositions and methods of this invention have been described in terms of particular embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide, exemplary procedural or other details supplementary to those set forth herein, are specifically incorporated herein by reference.

U.S. Pat. No. 5,738,110
U.S. Pat. No. 6,475,145
Aceves et al., *Gastrointest. Endosc. Clin. N Am.,* 18(1): 195-217, 2008.
Ackerman et al., In: *Eosinophils In Allergy and Inflammation,* Gleich and Kay (Eds.), Marcel Dekker, NY, 2:21-54, 1994.
Ackerman et al., *J Biol. Chem.,* 277:14859-68, 2002.
Ackerman et al., *J. Immunol.,* 125:2118-26, 1980.
Ackerman et al., *J Immunol.,* 127:1093-8, 1981.
Ackerman et al., *J. Immunol.,* 144:3961-9, 1990.
Ackerman et al., *J. Immunol.,* 150:456-68, 1993.
Arora and Yamazaki, *Clin. Gastroenterol. Hepatol.,* 2:523-30, 2004.
Ausubel et al., In: *Current Protocols in Molecular Biology,* John, Wiley & Sons, Inc, NY, 1994.
Bevilacqua et al., *Int. Arch. Allergy Immunol.,* 135:108-16, 2004.
Blanchard et al., *J Allergy Clin. Immunol.,* 118:1054-9, 2006c.
Blanchard et al., *J Clin. Invest.,* 116:536-47, 2006b.
Blanchard et al., *J Clin. Invest.,* 116:536-547, 2006a.

Desai et al., *Gastrointest. Endosc.,* 61:795-801, 2005.
Faubion et al., *J Pediatr. Gastroenterol. Nutr.,* 27:90-3, 1998.
Fiebiger et al., *J Exp. Med.,* 201:267-77, 2005.
Foroughi and Prussin, *Curr. Allergy Asthma Rep.,* 5:259-61, 2005.
Furuta *Am. J. Physiol. Gastrointest. Liver Physiol.,* 289: G890-7, 2005.
Furuta et al., *Gastroenterology,* 133:1342-63, 2007.
Furuta et al., *J Exp. Med.,* 193:1027-34, 2001.
Furuta et al., *J Leukoc. Bioi.,* 68:251-9, 2000.
Furuta, *Curr. Opin. Gastroenterol.,* 22:658-63, 2006.
Genta et al., *Adv. Anat. Pathol.,* 14:340-343, 2007.
Gomes et al., *J Allergy Clin. Immunol.,* 116:796-804, 2005.
Gonsalves et al., *Gastrointest. Endosc.,* 64:313-9, 2006.
Gowan et al., *Assay Drug Dev Technol.,* (3):391-401, 2007.
Gowan et al., *Assay Drug Dev. Techno/.,* 5:391-401, 2007.
Gracey et al., *Arch. Dis. Child.,* 52:74-6, 1977.
Gupta et al., *Am. J. Gastroenterol.,* 101:1125-8, 2006b.
Gupta et al., *Ear Nose Throat J.,* 84:632-3, 2005.
Gupta et al., *J. Pediatr. Gastroenterol. Nutr.,* 42:22-6, 2006a.
Hogan et al., *Curr. Allergy Asthma Rep.,* 6:65-71, 2006.
Isomoto et al., *Am. J. Gastroenterol.,* 99:589-97, 2004.
Kagalwalla et al., *Clin. Gastroenterol. Hepatol.,* 4:1097-102, 2006.
Karhausen et al., *J. Clin. Invest.,* 114:1098-106, 2004.
Kelly et al., *Gastroenterology,* 109:1503-12, 1995.
Kirsch et al., *J. Pediatr. Gastroenterol. Nutr.,* 44:20-6, 2007.
Konikoff et al., *Clin. Gastroenterol. Hepatol.,* 4:1328-36, 2006.
Li et al., *Gastroenterology,* 131:47-58, 2006.
Liacouras et al., *Clin. Gastroenterol. Hepatol.,* 3:1198-206, 2005.
Liacouras et al., *J. Pediatr. Gastroenterol. Nutr.,* 26:380-5, 1998.
Markowitz et al., *Am. J. Gastroenterol.,* 98:777-82, 2003.
Mekjavic and Rempel, *J. Appl. Physiol.,* 69:376-9, 1990.
Mishra et al., *Blood,* 96:1538-44, 2000.
Mishra et al., *J. Clin. Invest.,* 107:83-90, 2001.
Mishra et al., *J. Immunol.,* 168:2464-9, 2002.
Mishra et al., *J. Leukoc. Bioi.,* 81:916-24, 2007.
Montagnac et al., *J. Immunol.,* 174:5562-72, 2005a.
Montagnac et al., *Traffic,* 6:230-42, 2005b.
Ngo and Furuta, *Curr. Treat. Options Gastroenterol.,* 8:397-403, 2005.
Ngo et al., *Am. J. Gastroenterol.,* 101(7):1666-70, 2006.
Nurko et al., *J. Pediatr. Gastroenterol. Nutr.,* 38:436-41, 2004.
Oh et al., *Arch. Surg.,* 142:554-9; Dis. 559-60, 2007.
Plager et al., *J. Bioi. Chem.,* 274:14464-73, 1999.
Sabroe et al., *J. Allergy Clin. Immunol.,* 110:492-9, 2002.
Sambrook et al., In: *DNA microaarays: a molecular cloning manual,* Cold Spring Harbor Laboratory Press, Cold Spring Harbor, NY, 1989; 2001.
Savidge et al., *Gastroenterology,* 132(4):1344-58, 2007.
Spergel et al., *Ann. Allergy Asthma Immunol.,* 95:336-43, 2005.
Spergel et al., *J. Allergy Clin. Immunol.,* 109:363-8, 2002.
Spergel, *Clin. Exp. Allergy,* 35:1421-2, 2005.
Spergel, *Curr. Opin. Allergy Clin. Immunol.,* 7:274-8, 2007.
Stein et al., *J. Allergy Clin. Immunol.,* 118:1312-9, 2006.
Straumann et al., *Digestion,* 70:109-16, 2004.
Straumann et al., *Inflamm. Bowel Dis.,* 11:720-6, 2005.
Straumann et al., *J. Allergy Clin. Immunol.,* 108:954-61, 2001.
Sundaram et al., *J. Pediatr. Gastroenterol. Nutr.,* 38:208-12, 2004.
Teitelbaum et al., *Gastroenterology,* 122:1216-1225, 2002.
Thibeault et al., *Laryngoscope,* 117:2050-6, 2007.
Thomas et al., *S. Afr. Med. J.,* 48:2219-20, 1974.
Walsh et al., *Am. J. Surg. Pathol.,* 23:390-396, 1999.
Yoshida et al., *Scand. J. Gastroenterol.,* 39:816-22, 2004.
Yu et al., *Am. J. Physiol. Gastrointest. Liver Physiol.,* 285:G223-34, 2003.

What is claimed:

1. A device comprising a string having an esophageal segment, a capsule enclosing at least a portion of the string and having an opening, the string spanning the opening of the capsule, wherein the esophageal segment further comprises one or more capture agents.

2. The device according to claim 1, wherein the esophageal segment of the string comprises absorbent fiber, mesh fiber or textured fiber.

3. The device according to claim 1, wherein the string comprises an abrasive material.

4. The device according to claim 1, wherein the capsule is dissolvable.

5. The device according to claim 1, wherein the opening of the capsule is perforated.

6. The device according to claim 1, wherein the capsule comprises a base and a cap.

7. The device according to claim 1, wherein the string of the device is capable of being secured to a cheek of a subject when in use.

8. The device according to claim 1, wherein the one or more capture agents bind to one or more analytes.

9. The device according to claim 1, wherein the one or more capture agents comprise an antibody.

10. The device according to claim 1, further comprising one or more diagnostic or health indicators associated with or bound to the string after deployment in a subject.

11. The device according to claim 1, wherein the esophageal segment further comprises one or more diagnostic or health indicators associated with, or bound to, the one or more capture agents when the string is deployed in a subject, wherein the one or more diagnostic or health indicators comprise one or more of a major basic protein (MBP), an eosinophil cationic protein (ECP), an eosinophil peroxidase (EPO), an eosinophil-derived neurotoxin (EDN), CLC/Gal-10, other eosinophil granule protein, IL-6, IL-8, IL-1β, IL-5, INF-γ and other cytokines, a chemokine, a cellular infiltrate, pH, IgE, tryptase, other marker of an allergic response, a receptor molecule, an allergen, arachadonic acid products, other inflammatory marker, substance P, bradykinin, other neurotransmitter, eosinophils, leukotrienes, other mast cells, squamous epithelial cells, inflammatory cells, bacteria, yeast, other microorganisms, and nucleic acids or polypeptides from a microorganism.

12. A kit comprising the device according to claim 1 and at least one container.

13. A method for analyzing gastrointestinal microbiota of a subject, the method comprising: deploying the device according to claim 1 into a gastrointestinal tract of the subject; retrieving the device and analyzing the device for captured diagnostic or health indicators from the gastrointestinal tract.

14. The method according to claim 13, assessing condition of the subject based on the captured diagnostic or health indicators.

15. The device according to claim 1, wherein the string is a nylon fiber string.

16. The device according to claim 1, wherein the device does not include drag material in the capsule.

17. The device according to claim 1, wherein when deployed the esophageal segment of the string is located in an esophagus of a subject.

18. The device according to claim 1, wherein the one or more capture agents are positioned on the esophageal segment of the string such that the one or more capture agents remain exposed to a gastrointestinal tract of a subject during withdrawal of the string from the subject.

19. The device according to claim 1, wherein the one or more capture agents are positioned on the esophageal segment of the string such that the one or more capture agents are targeted to bind to one or more diagnostic or health indicators from an esophagus of a subject.

20. The device according to claim 19, wherein when the one or more diagnostic or health indicators bind to the one or more capture agents, the one or more diagnostic or health indicators bound to the one or more capture agents remain exposed to a gastrointestinal tract of the subject during withdrawal of the string from the subject.

* * * * *